(12) United States Patent
Torres et al.

(10) Patent No.: US 10,913,750 B2
(45) Date of Patent: Feb. 9, 2021

(54) TUBULIN-BINDING COMPOUNDS, COMPOSITIONS AND USES RELATED THERETO

(71) Applicant: The Regents of the University of California, Oakland, CA (US)

(72) Inventors: Jorge Torres, Los Angeles, CA (US); Robert Damoiseaux, Los Angeles, CA (US); Todd O. Yeates, Los Angeles, CA (US); Silvia Senese, Los Angeles, CA (US); Dan E. McNamara, Los Angeles, CA (US); Yu-Chen Lo, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/573,602

(22) Filed: Sep. 17, 2019

(65) Prior Publication Data

US 2020/0079789 A1 Mar. 12, 2020

Related U.S. Application Data

(62) Division of application No. 15/577,551, filed as application No. PCT/US2016/034286 on May 26, 2016.

(60) Provisional application No. 62/191,738, filed on Jul. 13, 2015, provisional application No. 62/167,526, filed on May 28, 2015.

(51) Int. Cl.
| | |
|---|---|
| *C07D 417/06* | (2006.01) |
| *A61P 35/00* | (2006.01) |
| *C07D 495/04* | (2006.01) |
| *C07D 471/04* | (2006.01) |
| *C07D 487/04* | (2006.01) |
| *C07D 277/64* | (2006.01) |

(52) U.S. Cl.
CPC ............ *C07D 495/04* (2013.01); *A61P 35/00* (2018.01); *C07D 277/64* (2013.01); *C07D 417/06* (2013.01); *C07D 471/04* (2013.01); *C07D 487/04* (2013.01)

(58) Field of Classification Search
CPC .................................................. C07D 417/06
See application file for complete search history.

(56) References Cited

FOREIGN PATENT DOCUMENTS

| DE | 225993 A1 | 8/1985 |
| WO | WO-2010/006032 A1 | 1/2010 |
| WO | WO-2011/127192 A2 | 10/2011 |
| WO | WO-2012/119605 A1 | 9/2012 |
| WO | WO-2015/051188 A1 | 4/2015 |
| WO | WO-2016/191537 A1 | 12/2016 |

OTHER PUBLICATIONS

Cancer Drug Design and Discovery, Neidle, Stephen,ed. (Elsevier/Academic Press), pp. 427-431 (2008). (Year: 2008).*
Yamazaki et al. Melanoma Res. p. 1-16 Published online Dec. 23, 2014. Available online at https://www.ncbi.nlm.nih.gov/pmc/articles/PMC4276568/ 1. (Year: 2014).*
Abbas et al., "Synthesis, antitumor and antibacterial activities of some novel tetrahydrobenzo[4,5]thieno[2,3-d]pyrimidine derivatives," Euro J Med Chem, 65:195-204 (2013).
Aurora Product Guide, http://ww.aurorafinechemicals.com/about.html (2015).
CAS Registry No. 733760-81-1, dated Aug. 27, 2004.
CAS Registry No. 897287-01-3, dated Jul. 28, 2006.
CAS Registry No. 744226-55-9, dated Sep. 14, 2004.
CAS Registry No. 745796-58-1, dated Sep. 16, 2004.
CAS Registry No. 797025-57-1, dated Dec. 14, 2004.
Dudhe et al., "Synthesis and biological evaluation of novel condensed pyrimidinylmethylsulfinylbenzimidazoles as antiulcer agent," Medicinal Chemistry Research, 22(8):3719-3727 (2012).
Extended European Search Report Received for EP Patent Application No. EP16800699, dated Feb. 13, 2019.
International Search Report and Written Opinion for International Application No. PCT/US2016/034286 dated Sep. 4, 2016.
Kamal et al., "Synthesis of arylpyrazole linked benzimidazole conjugates as potential microtubule disruptors," Bioorg Med Chem, 23(5):1082-1095 (2015).
Mavorva et al., "Synthesis and antiproliferative activity of some new thieno[2,3-d]pyrimidin-4{3H}-ones containing 1, 2, 4-triazole and 1, 3, 4-thiadiazole moiety," European Journal of Medicinal Chemistry, 86:6760683 (2014).
McNamara et al., "Structures of potent anticancer compounds bound to tubulin," Protein Sci, 24(7):1164-1172 (2015).
Rai et al., "CXI-benzo-84 reversibly binds to tubulin at colchicine site and induces apoptosis in cancer cells," Biochem Pharmacol, 86(3):378-391 (2013).
Ryabukhin et al., "Combinatorial Knoevenagel Reactions," Journal of Combinatorial Chemistry, 9(6):1073-1078 (2007).

(Continued)

*Primary Examiner* — Emily A Bernhardt
(74) *Attorney, Agent, or Firm* — Foley Hoag LLP; David P. Halstead; Lucas P. Watkins

(57) ABSTRACT

This disclosure relates to methods of treating cancer (e.g., melanoma) with

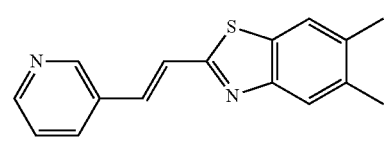

(MI-181).

4 Claims, 18 Drawing Sheets

(56) References Cited

OTHER PUBLICATIONS

Senese et al., "Chemical dissection of the cell cycle: probes for cell biology and anti-cancer drug development," Cell Death Di, 5:e1462 (2014).

Shishoo et al., "Studies on the synthesis of 2-(2-Arylvinyl)Thieno not 2, 3-D 3/4 Pyrmidinesand 5-(2-Arylvinyl) Triazolothienol not 3, 2-E 3/4 Pyrimidines," Journal of Heterocyclic Chemistry, 22(3):825-830 (1985).

Sundaram et al., "Characterization of a brain permeant fluorescent molecule and visualization of Aβ parenchymal plaques, using real-time multiphoton imaging in transgenic mice," Org Lett, 16(14):3640-3643 (2014).

* cited by examiner

| | | | |
|---|---|---|---|
| % G1 | 56.9 | 20.3 | 24.3 |
| % S | 9.3 | 10.6 | 9.6 |
| % G2/M | 31.6 | 63.6 | 62.1 |

TUBULIN-BINDING COMPOUNDS, COMPOSITIONS AND USES RELATED THERETO

REFERENCE TO RELATED APPLICATIONS

This application is a divisional of U.S. application Ser. No. 15/577,551, filed Nov. 28, 2017, which is the U.S. National Stage of International Patent Application No. PCT/US2016/034286, filed May 26, 2016, which claims the benefit of U.S. Provisional Patent Application No. 62/167,526, filed May 28, 2015, and U.S. Provisional Patent Application No. 62/191,738, filed Jul. 13, 2015, the contents of each of which are fully incorporated by reference herein in their entirety.

STATEMENT REGARDING FEDERALLY SPONSORED RESEARCH OR DEVELOPMENT

This invention was made with Government support under TR000124 and CA016042, awarded by the National Institutes of Health. The Government has certain rights in the invention.

FIELD OF THE DISCLOSURE

This disclosure relates to compounds useful in compositions and methods for treating hyperproliferative disorders, including cancers.

BACKGROUND OF THE INVENTION

The cell cycle is a set of coordinated events that culminate in the formation of two cells from one mother cell. It is composed of four major phases; G1 (growth phase 1), S (DNA synthesis phase), G2 (growth phase 2) and M (mitosis), which function to integrate environment sensing signaling pathways with cell growth and proliferation. (Schwartz G. K., Shah M. A. Targeting the cell cycle: a new approach to cancer therapy. *J Clin Oncol* 2005, 23(36): 9408-9421.) Cancer cells often deregulate the cell cycle and undergo unscheduled cell divisions. Therefore, inhibition of the the cell cycle represents an opportunity for therapeutic intervention in treating proliferative diseases like cancer. (Williams G. H., Stoeber K. The cell cycle and cancer. *J Pathol* 2012, 226(2): 352-364.) Most anticancer drugs perturb the proliferation cycle of tumor cells by inhibiting/damaging cell cycle events, which activate checkpoints, arrest cells and induce apoptosis. (Manchado, E., et al., Killing cells by targeting mitosis. *Cell Death Differ* 2012, 19, (3), 369-77.) For example, inhibitors targeting DNA replication (5-fluorouracil) and cell division (microtubule-stabilizing paclitaxel) have been used successfully for treating a broad array of cancers including breast and colorectal. (Williams, op. cit.)

Many anticancer drugs perturb the proliferation cycle of tumor cells. These drugs are broadly classified into those acting in interphase, such as DNA damaging agents, and those acting in mitosis, so-called antimitotic drugs. Antimitotics are a group of natural and synthetic small molecules that function by activating the spindle assembly checkpoint (SAC), which arrests cells in mitosis until proper microtubule-kinetochore attachment occurs. (Gascoigne, K E et al., Cancer cells display profound intra- and interline variation following prolonged exposure to antimitotic drugs. *Cancer Cell* 2008, 14, (2), 111-22; Shi, J., et al., Cell type variation in responses to antimitotic drugs that target microtubules and kinesin-5. *Cancer Res* 2008, 68, (9), 3269-76.) Prolonged mitotic arrest activates an apoptotic response leading to cell death. (Matson, D. R.; Stukenberg, P. T., Spindle poisons and cell fate: a tale of two pathways. *Mol Interv* 2011, 11, (2), 141-50.) This process occurs through p38, JNK, and CKII kinase mediated phosphorylation of Mcl1, which targets Mcl1 for ubiquitination by the SCF-Fbw7 ubiquitin ligase and proteosome-dependent degradation. (Matson op. cit.; Wertz, I. E., et al., Sensitivity to anitubulin chemotherapeutics is regulated by MCL1 and FBW7. *Nature* 2011, 471, (7336), 100-4.; Manchado, op. cit.) Mcl1 destruction relieves its inhibiton of Bax and Bak (pro-apoptotic factors), allowing them to bind the mitochondrial outer membrane to induce an apoptotic cell death. (Matson; Wertz; Manchado, op. cit.)

Current antimitotics work through binding and inhibition of three major classes of molecules; microtubules, kinases, and kinesins. (Manchado, op. cit.) For example, GSK-461363, a polo like kinase 1 (Plk1) ATP-competitive inhibitor, blocks Plk1-dependent centrosome maturation, which arrests cells in prophase with a monopolar spindle. (Lansing, T. J., et al., In vitro biological activity of a novel small-molecule inhibitor of polo-like kinase 1. *Mol Cancer Ther* 2007, 6, (2), 450-9.) Similarly, Ispinesib, an allosteric inhibitor of Kinesin-5 arrests cells with a monopolar spindle, due to the inability of Kinesin-5 to separate centrosomes to opposite ends of the cell. (Kapoor, T. M., et al., Probing spindle assembly mechanisms with monastrol, a small moelcule inhibitor of the mitotic kinesisn, Eg5. *J Cell Biol,* 2000, 150, (5), 975-88.) Microtubule targeting agents including stabilizers (taxanes like paclitaxel (taxol) and epothilones) and destabilizers (vinca alkaloids and colchicine) bind to tubulin and perturb microtubule dynamics by stabilizing or destabilizing microtubules and thereby their ability to align and segregate chromosomes. (Dumontet, C.; Jordan, M. A., Microtuble-binding agents: a dynamic field of cancer therapeutics. *Nat Rev Drug Discov* 2010, 9, (10), 790-803.) Although microtubule-targeting agents are some of the most common chemotherapeutic agents used to treat a wide variety of cancers, they show important dose-limiting toxicities, including neutropenia and neurotoxicity, largely a consequence of disturbing microtubule dynamics in neurons. (Canta, A., et al., Tubulin: a target for antineoplastic drugs into the cancer cells but also in the periperal nervous system. *Curr Med Chem* 2009, 16, (11), 1315-24; Carlson, K., Ocean, A. J., Peripheral neuropathy with microtubule-targeting agents: occurrence and management approach. *Clin Breast Cancer* 2011, 11 (2), 73-81.) Most of the microtubule-targeting agents used clinically are large, natural (difficult to synthesize), hydrophobic compounds with limited solubility. In addition, some cancers acquire resistance to these agents by overexpressing efflux pumps like MDR1, mutating key amino acids in $\beta$I-tubulin, or by overexpressing $\beta$III-tubulin. (Rivera, E., Gomez, H., Chemotherapy resistance in metastatic breast cancer: the evolving role of ixabepilone. *Breast Cancer Res* 2010, 12 Suppl 2, S2.) Thus, there is a critical need to identify novel tubulin-targeting drugs with improved properties that can be used as anti-cancer agents.

An inhibitor of the M-phase of the cell cycle is M-181, which targets tubulin. Characterization experiments revealed inhibition of tubulin polymerization, spindle assembly checkpoint (SAC) activation, mitotic arrest, and induction of apoptosis in cells treated with MI-181. (Senese, S., et al., Chemical dissection of the cell cycle: probes for cell biology and anti-cancer drug development. *Cell Death & Disease,* 2014, 5, e1462; published online 16 October 2014).

Furthermore, there is a need for new antimitotic compounds, with colchicine-like properties, that bind to tubulin and are useful in therapeutic preparations for the treatment of disorders responsive to inhibition of microtubule polymerization, including hyperproliferative disorders such as cancers and myelodysplastic syndromes.

SUMMARY OF THE DISCLOSURE

The present disclosure addresses the aforementioned need by providing a novel class of compounds that inhibit cell proliferation. In certain embodiments, these compounds bind to tubulin, to inhibit microtubule polymerization, arrest cells in mitosis, activate the spindle assembly checkpoint, and/or trigger an apoptotic cell death. In some embodiments, the compounds of this disclosure represent a novel class of compounds that bind β-tubulin.

In one aspect, this disclosure provides compounds of Formula I:

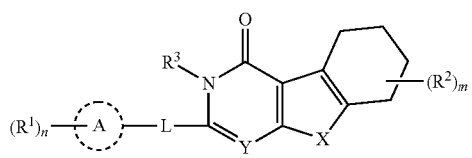

I wherein the variables are as defined herein. The compounds are typically selective modulators of the microtubules. In some embodiments, the compounds as described herein bind to microtubulin. In some embodiments, the compounds as described herein inhibit microtubule polymerization, arrest cells in mitosis, induce apoptosis, and/or cause cell death. Compounds of Formula I can be used to treat the conditions as described herein.

Another aspect of this disclosure provides compounds of Formula II:

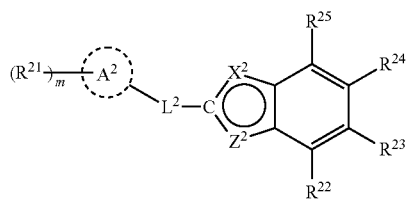

II wherein the variables are as defined herein. The compounds are typically selective modulators of microtubules. In some embodiments, the compounds as described herein bind to microtubulin. In some embodiments, the compounds as described herein inhibit microtubule polymerization, arrest cells in mitosis, induce apoptosis, and/or cause cell death. Compounds of Formula I can be used to treat the conditions as described herein.

Another aspect of this disclosure provides compositions (such as pharmaceutical compositions) that comprise the compounds of this disclosure. The disclosure also includes the use of the compounds or compositions disclosed herein in the manufacture of a medicament for the treatment of one or more of the conditions described herein.

Another aspect of this disclosure provides methods for treating a myelodysplastic syndrome (MDS) in a subject in need thereof using a compound described herein. In some embodiments, the myelodysplastic syndrome that may be treated by a compound described herein is selected from, but not limited to, refractory anemia, refractory anemia with ringed sideroblasts, refractory anemia with excess blasts, refractory anemia with excess blasts in transformation, and chronic myelomonocytic leukemia.

Another aspect of this disclosure provides methods for treating the conditions described herein using the compounds or compositions disclosed herein, including methods for treating cancer in a subject in need or at risk thereof. In some embodiments, the cancer that may be treated by a compound or composition described herein is selected from, but not limited to, ovarian cancer, cervical cancer, brain cancer, lung cancer, skin cancer, colorectal cancer, esophageal cancer, breast cancer, prostate cancer, leukemia, multiple myeloma, bone cancer, pancreatic cancer, bladder cancer, endometrial cancer, kidney cancer, liver cancer, eye cancer, pituitary cancer, testicular cancer, and stomach cancer.

Another aspect of this disclosure provides methods for treating a skin cancer in a subject in need thereof using a compound described herein. In some embodiments, the skin cancer that may be treated by a compound described herein is a melanoma. In some embodiments, the melanoma is selected from, but not limited to, lentigo maligna melanoma, superficial spreading melanoma, acral lentiginous melanoma, mucosal melanoma, nodular melanoma, polypoid melanoma, desmoplastic melanoma, amelanotic melanoma, soft-tissue melanoma, melanoma with small nevus-like cells, melanoma with features of a Spitz nevus, and uveal melanoma.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 4B shows the drug response dose curves to measure mitotic arrest $IC_{50}$s for increasing treatment with compound 10a.

FIG. 6B shows the cell viability IC$_{50}$ for patient-derived glioblastoma cells treated with compound 10a.

DETAILED DESCRIPTION

Compounds

Figure 1A:
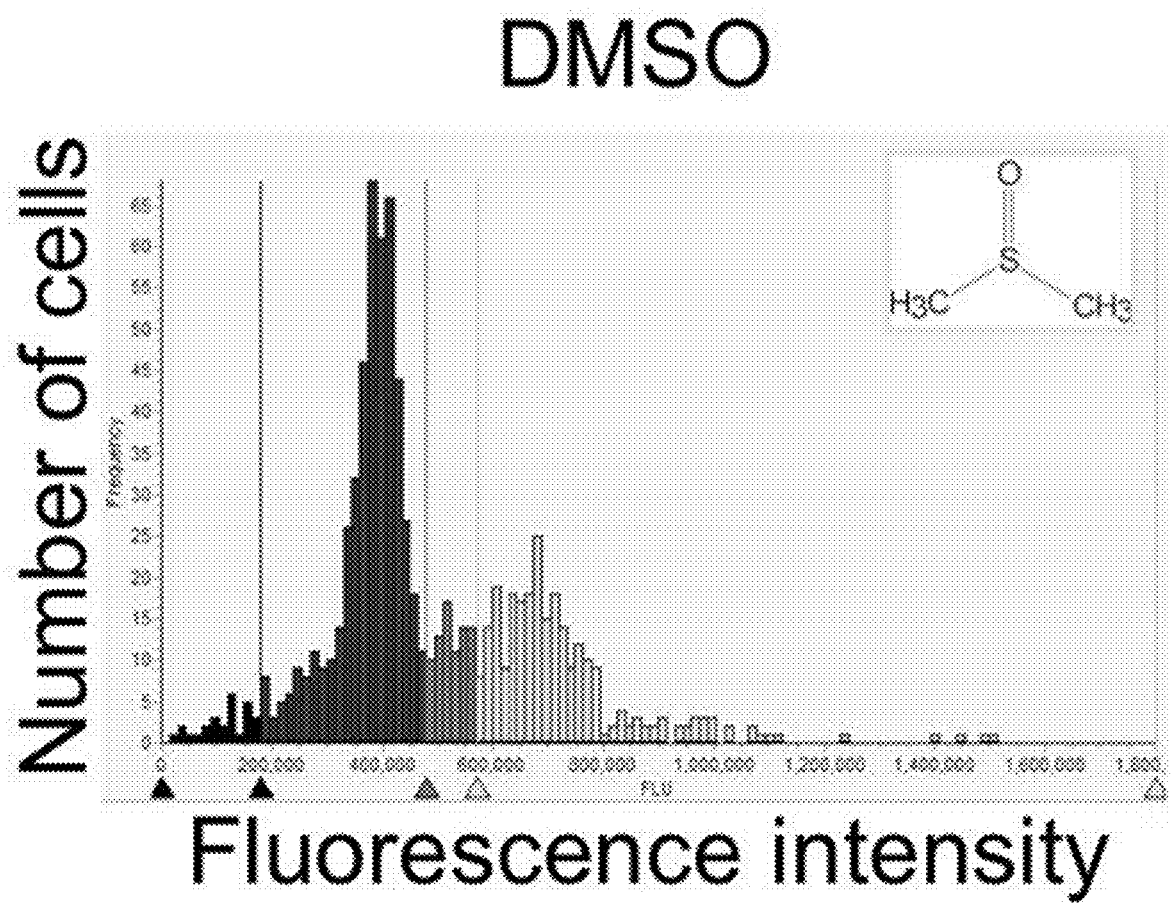
FIG. 1A shows that the cell cycle histogram of HeLa cells treated with DMSO for 20 hours. The percentage of cells in G1 phase, S phase and G2/M phase is indicated below the histogram for each treatment.

In one aspect, the present disclosure provides a compound of Formula I:

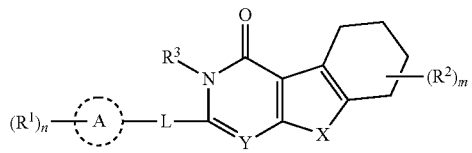

I or a pharmaceutically acceptable salt thereof, wherein:
X is —NH—, —O— or —S—, preferably —S—;
Y is —CH= or —N=, preferably —N=;
n is selected from 0-5;
m is selected from 0-5;
A is a ring selected from (C6-C10)-aryl and 5-10-membered heteroaryl;
L is a C1-C3 straight or branched carbon chain that may be fully saturated, or have one or
more units of unsaturation, and links A to the central ring, wherein one or more methylene units of L are optionally and independently replaced by —O— —S—, —S(O)—, —S(O)$_2$—, —N=, or —NH—, wherein L is optionally further substituted with one or more R$^4$, preferably L is chosen such that L interposes 2 atoms between the central ring (bearing R$^3$) and ring A, e.g., substituted or unsubstituted ethylene or ethenylene (vinylene);
each occurrence of R$^1$ is independently selected from:
halogen (preferably —F), nitro, cyano, hydroxyl, thiol, amino, alkyl (preferably lower alkyl, such as methyl or ethyl), haloalkyl (such as —CF$_3$), alkoxy (such as methoxy or ethoxy), haloalkoxy (such as —OCF$_3$ and —OCHF$_2$), alkylamino, alkylthio (such as —SCH$_3$), hydroxyalkyl, alkoxyalkyl, aminoalkyl, thioether, ester, amide, thioester, carboxy, carbonate, carbamate, urea, sulfonate, sulfone, sulfoxide, sulfonamide, sulfate, acyl, acyloxy, and acylamino;

each occurrence of R$^2$ is independently selected from alkyl (preferably lower alkyl, such as methyl) and halogen;
R$^3$ is hydrogen or alkyl, preferably hydrogen;
each occurrence of R$^4$ is independently selected from:
cyano, halogen, nitro, hydroxyl, thiol, amino, alkyl, haloalkyl, alkoxy, haloalkoxy, alkylamino, alkylthio, hydroxyalkyl, alkoxyalkyl, aminoalkyl, thioether, ester, amide, thioester, carboxy, carbonate, carbamate, urea, sulfonate, sulfone, sulfoxide, sulfonamide, sulfate, acyl, acyloxy, and acylamino.

In some embodiments of Formula I, L is chosen such that L interposes 2 atoms between the central ring (bearing R$^3$) and ring A, e.g., substituted or unsubstituted ethylene or ethenylene (vinylene). In some embodiments, L is selected from: —CH$_2$—, —CH$_2$SCH$_2$—, —CH$_2$CH$_2$S—, —SCH$_2$CH$_2$—, —CH$_2$OCH$_2$—, —CH$_2$CH$_2$O—, —OCH$_2$CH$_2$—, —CH$_2$NHCH$_2$—, —CH$_2$CH$_2$NH—, —NHCH$_2$CH$_2$—, —CH$_2$CH$_2$—, —CH$_2$CH$_2$CH$_2$—, —CH$_2$S—, —SCH$_2$—, —CH$_2$O—, —OCH$_2$—, —CH$_2$NH—, —NHCH$_2$—, and —CH=CH—, preferably —CH=CH—, wherein any hydrogen atom of a CH or CH$_2$ unit may optionally be replaced by R$^4$ (such as lower alkyl), any hydrogen of an NH unit may optionally be replaced by R$^4$ (such as lower alkyl).

In some embodiments of Formula I, L is —CH=CH—. In certain embodiments, the compound of Formula I has a structure of formula IA:

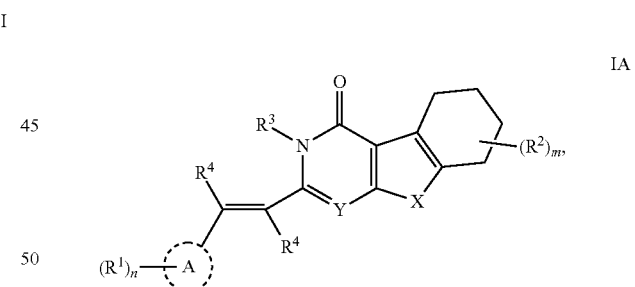

IA wherein X, Y, n, m, A, R$^1$, R$^2$, R$^3$ and R$^4$ are as defined herein. In some embodiments of a compound of formula IA, each occurrence of R$^4$ is independently selected from hydrogen or lower alkyl (e.g., methyl or ethyl). In some embodiments of a compound of formula IA, both occurrences of R$^4$ are hydrogen.

In some embodiments of Formula I, Y is —N=. In some embodiments, X is —S—. In some embodiments, X is —S— and Y is —N=.

In some embodiments of Formula I, A is unsubstituted or substituted (C6-C10)-aryl, such as unsubstituted or substituted phenyl. In some embodiments, the compound of Formula I has a structure of formula IA-1:

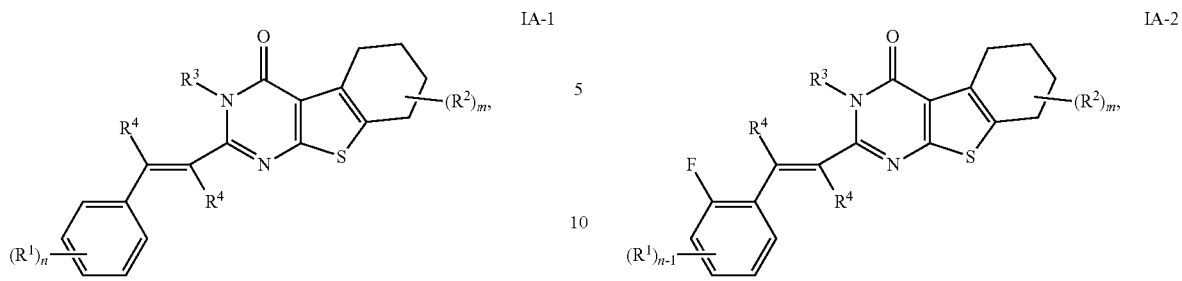

wherein the variables are as defined herein. For example, in some embodiments, A (and/or the phenyl ring bearing $R^1$) is selected from:

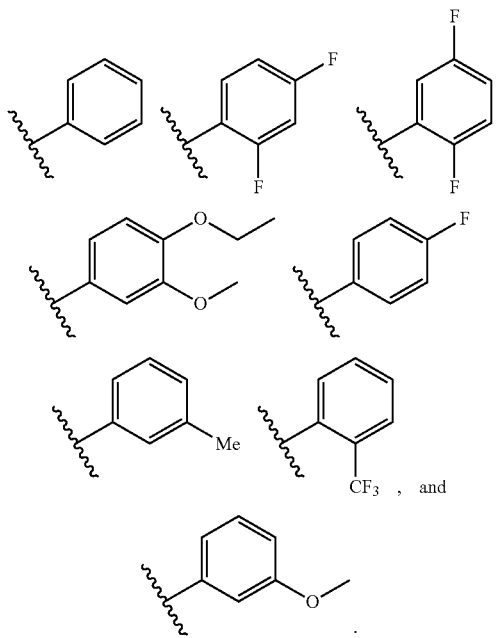

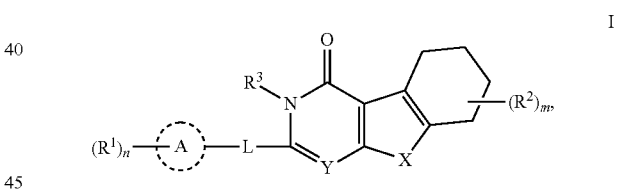

In some embodiments of Formula I, n is 0-3, preferably 0, 1 or 2. In some embodiments, n is 0. In some embodiments, n is 1. In other embodiments, n is 2.

In some embodiment of Formula I s, each occurrence of $R^1$, when present, is independently selected from: halogen, lower alkyl, haloalkyl, alkoxy, haloalkoxy, and alkylthio. In some embodiments, when present, each occurrence of $R^1$ is independently selected from: —F, —Br, —Cl, -Me, -Et, —$CF_3$, —OMe, —OEt, —$OCF_3$, —$OCHF_2$, and —SMe. In some embodiments, each occurrence of $R^1$ is independently selected from: —F, -Me, —$CF_3$, —OMe, and —OEt.

In some embodiments of Formula I, n is 1-3, and at least one $R^1$ is —F. In some embodiments, n is 1 or 2, and at least one $R^1$ is —F. In some embodiments, n is 2 and both $R^1$ are —F.

In some embodiments of Formula I, the compound has a structure of formula IA-2:

wherein the variables are as defined herein. In some embodiments of a compound of formula IA-2, n is 1. In some embodiments of a compound of formula IA-2, n is 2. In some embodiments of a compound of formula IA-2, n is 2 and $R^1$ is —F.

In some embodiments of Formula I, $R^3$ is hydrogen or lower alkyl (such as methyl or ethyl). In some embodiments, $R^3$ is hydrogen.

In some embodiments of Formula I, m is 0-3, preferably 0, 1 or 2. In some embodiments, m is 0. In some embodiments, m is 1. In other embodiments, m is 2.

In some embodiments of Formula I, when present, each occurrence of $R^4$ is independently hydrogen or lower alkyl (such as methyl or ethyl).

The disclosure also includes various combinations of n, m, L, A, X, Y, $R^1$, $R^2$, $R^3$ and $R^4$ as described above. These combinations can in turn be combined with any or all of the values of the other variables described above. For example, in some embodiments, the compound of this disclosure has a structure of Formula I:

wherein: X is —S—; Y is —N=; n is 0, 1 or 2; m is 0, 1 or 2, preferably 0; A is (C6-C10)-aryl-, preferably phenyl; L is ethylene or ethenylene (vinylene), preferably —CH=CH—, wherein L is optionally substituted with one or more $R^4$; each occurrence of $R^1$ is independently selected from: halogen, lower alkyl, haloalkyl, and alkoxy, preferably selected from —F, -Me, —$CF_3$, —OMe, and —OE; each occurrence of $R^2$ is independently selected from lower alkyl and halogen; $R^3$ is hydrogen or lower alkyl, preferably hydrogen; and each occurrence of $R^4$ is independently hydrogen or lower alkyl, preferably hydrogen. In some of such embodiments, m is 0; A is phenyl; L is ethenylene (vinylene), preferably —CH=CH—; and each occurrence of $R^1$ is independently selected from: —F, -Me, —$CF_3$, —OMe, and —OEt; and $R^3$ is hydrogen.

In some embodiments, the compound has a structure of formula IA:

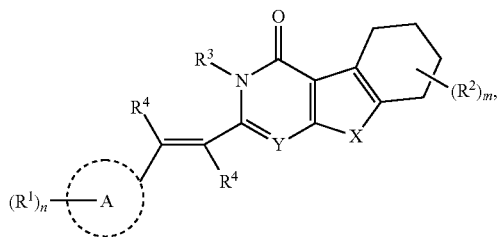

IA wherein: X is —S—; Y is —N═; n is 0, 1 or 2; m is 0, 1 or 2, preferably 0; A is (C6-C10)-aryl-, preferably phenyl; each occurrence of R¹ is independently selected from: halogen, lower alkyl, haloakyl, and alkoxy, preferably selected from selected from: —F, -Me, —CF₃, —OMe, and —OEt; each occurrence of R² is independently selected from lower alkyl and halogen; R³ is hydrogen or lower alkyl, preferably hydrogen; and each occurrence of R⁴ is independently hydrogen or lower alkyl, preferably hydrogen. In some of such embodiments, m is 0; A is phenyl; each occurrence of R¹ is independently selected from: —F, -Me, —CF₃, —OMe, and —OEt; R³ is hydrogen; and each occurrence of R⁴ is hydrogen.

In some embodiments, the compound of Formula IA is selected from:

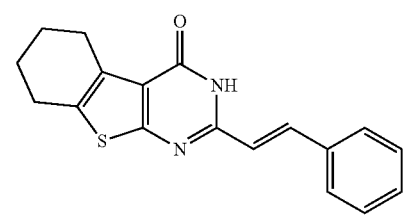

10a

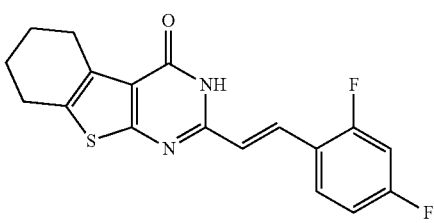

10b

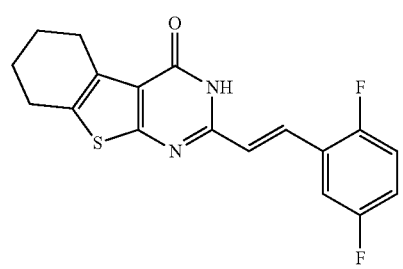

10f

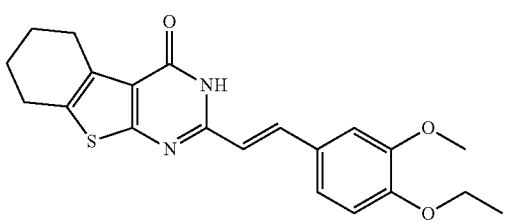

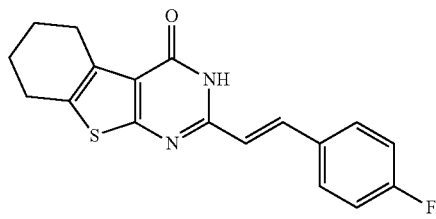

10c

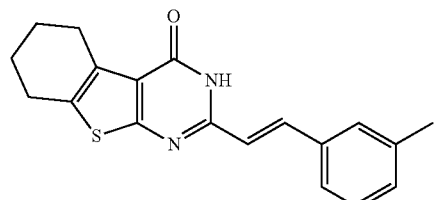

10g

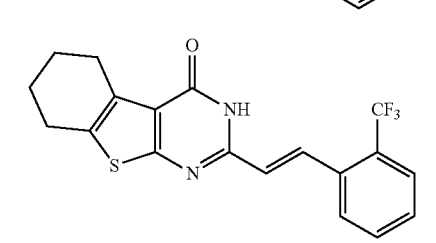

10u

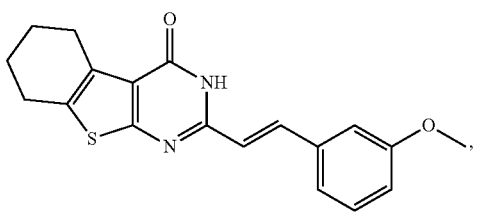

10d or a pharmaceutically acceptable salt thereof.

In another aspect, the present disclosure provides a compound of Formula II:

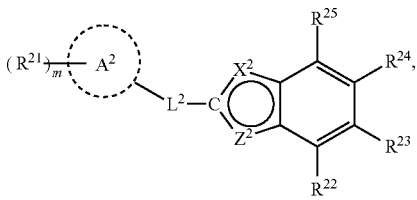

II or a pharmaceutically acceptable salt thereof, wherein:

X is —N═;

Z is —NH—, —O—, or —S—;

R²¹, independently for each occurrence, is selected from hydroxyl, halogen, cyano, substituted or unsubstituted amido, amino, acyl, alkyl, alkenyl, alkynyl, aryl, aralkyl, cycloalkyl, cycloalkylalkyl, heterocyclyl, heterocycloalkyl, acylamino, alkylamino, carbamate, ester, heteroaryl, heteroaralkyl, carbamate, sulfonyl, sulfoxido, sulfamoyl, and sulfonamido;

R²², R²³, R²⁴, R²⁵, independently for each occurrence, are selected from H, hydroxyl, halogen, cyano, substituted or unsubstituted amido, amino, acyl, alkyl, alkenyl, alkynyl, aryl, aralkyl, cycloalkyl, cycloalkylalkyl, heterocyclyl, heterocycloalkyl, acylamino, alkylamino, carbamate, ester, heteroaryl, heteroaralkyl, carbamate, sulfonyl, sulfoxido, sulfamoyl, and sulfonamido;

$L^2$ is absent or selected from —S—, substituted or unsubstituted alkyl, alkenyl, alkynyl, and heteroaryl;

$A^2$ is a ring selected from substituted or unsubstituted aryl or heteroaryl; and m is selected from 0-5.

In some embodiments of Formula II, $L^2$ is a substituted or unsubstituted alkenyl group.

In some embodiments of Formula II, $R^{22}$ and $R^{25}$ are both hydrogen.

In some embodiments of Formula II, $Z^2$ is S.

In some embodiments of Formula II, $A^2$ is pyridyl, such as pyridin-3-yl.

In some embodiments of Formula II, $R^{23}$ and $R^{24}$ are both substituted or unsubstituted alkyl.

In some embodiments of Formula II, m is 0.

In some embodiments, the compound of Formula II is MI-181:

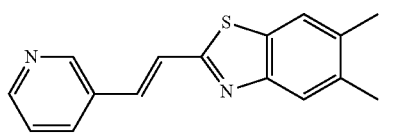 [SMILES: Cc1cc2nc(/C=C/c3cccnc3)sc2cc1C]

MI-181

In another aspect, the present disclosure provides a pharmaceutical composition comprising a compound of this disclosure, and a pharmaceutically acceptable carrier, adjuvant or vehicle.

In another aspect, the present disclosure provides a method for treating cancer in a subject in need thereof, comprising administering to the subject an effective amount of a compound of this disclosure. In some such embodiments, the subject is a mammal, such as a human.

In another aspect, the present disclosure provides a method of modulating microtubules in a cell, comprising contacting the cell with a compound of this disclosure.

In some embodiments, the compounds of this disclosure are more soluble in aqueous solutions, as compared to paclitaxel. In some embodiments, the compounds of this disclosure have a log S of −8.4319 or higher. In some embodiments, the compounds of this disclosure have a log S selected from −4.0 to −8.5. In some embodiments, the compounds of this disclosure have a log S selected from −5.0 to −6.0.

In some embodiments, the compounds of this disclosure are highly soluble in aqueous saline solutions, such as phosphate buffered saline (PBS). In such embodiments, the compounds of this disclosure can be delivered or administered as a solution or suspension in aqueous saline solutions, without any additional delivery vehicles (such as the Cremophor EL® formulation). In some embodiments, the compounds of this disclosure can be administered orally.

In some embodiments, the compounds of this disclosure can effectively pass the blood brain barrier when administered, e.g., for treating brain cancers.

In some embodiments, the compounds of this disclosure bind to all tubulin isoforms. In some embodiments, the compounds described herein are effective in treating paclitaxel-resistant cancers that overexpress β-tubulin isoform 3.

Many types of cancers evade anticancer drug killing by overexpressing efflux pumps that actively shuttle the drug out of the cell and thus lowering the active intracellular concentration of the drug and its ability to kill the cell. For example, the P-glycoprotein (P-gp) efflux pump (a product of the multidrug resistant gene MDR1) can transport paclitaxel out of the cell, thus rendering it ineffective. See, e.g., Gottesman M M (2002) Mechanisms of cancer drug resistance. Annu Rev Med 53: 615-627. Thus, P-gp overexpressing cancers are resistant to paclitaxel. In some embodiments, compounds of the disclosure are not substrates of these pumps and thus are effective against cancers that overexpress drug efflux pumps.

In certain embodiments, the subject compounds are effective in paclitaxel-resistant cancers that have become resistant to paclitaxel due to mutagenesis of the β-tubulin taxane-binding site.

In another aspect, the present disclosure provides a pharmaceutical composition comprising a pharmaceutically acceptable carrier and a compound of this disclosure. Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose based substances, polyethylene glycol, sodium carboxymethylcellulose, polyacrylates, waxes, polyethylene polyoxypropylene block polymers, polyethylene glycol and wool fat.

General Synthetic Methodology

The compounds of this disclosure may be prepared in general by methods known to those skilled in the art. Illustrated herein are general and synthetic routes to the compounds of the present disclosure. Other equivalent routes, which will be readily apparent to the ordinary skilled organic chemist, may alternatively be used to synthesize various portions of the molecules as illustrated herein.

Uses of the Compounds

The present disclosure provides novel compounds of Formulas I, IA, IA-1, IA-2, and II, as well as salts and prodrugs thereof, which, together with the specific microtubule-inhibiting compounds disclosed herein, are the compounds of the disclosure. Accordingly, the present invention includes all uses of the compounds of the disclosure, including their use in compositions (such as pharmaceutical compositions) and therapeutic methods (e.g., for modulating cell division and other uses disclosed herein), as well as uses in diagnostic assays and as research tools.

The compounds of the disclosure are useful in modulating microtubules, including destabilizing microtubules and/or inhibiting mitotic spindle formation, for the treatment of various conditions such as all proliferative disorders as mentioned above. Accordingly, the invention provides a method of modulating microtubules' stability and/or mitotic spindle formation, by administering an effective amount of a compound of the disclosure to a cell or subject in need thereof. In a further aspect, the invention provides a method of destabilizing microtubules and/or inhibiting mitotic spindle formation, by administering an effective amount of a compound of the disclosure to a cell or subject in need thereof.

While the compounds of the disclosure may act by destabilizing microtubules in a cell or subject in need thereof, one of skill in the art will appreciate that other modes or mechanisms of action for the compounds of the disclosure are possible.

In one aspect, the present invention provides a method for modulating cell division and/or proliferation, comprising administering an effective amount of a compound of the disclosure to a cell or subject in need thereof. In some embodiments, the invention provides a method of arresting cells during the process of cell division (mitosis), inducing apoptosis, and/or causing cell death, the method comprising administering an effective amount of a compound of the disclosure to a cell or subject in need thereof. In particular, the method of the disclosure is useful in inhibiting the division and/or proliferation of abnormal but not normal cells. Abnormal cells include any type of cell that is causative of or involved in a disease or condition and wherein it is desirable to modulate or inhibit the proliferation of the abnormal cell to treat the disease or condition. Examples of abnormal cells include malignant or cancerous cells as well as cell that over-proliferate in inflammatory conditions.

In some embodiments, the compounds of the disclosure are effective at killing cancer cells while at the same time they do not kill normal cells. These properties make the compounds of the disclosure useful as anti-cancer agents. Accordingly, in some embodiments, the present invention provides a method of inhibiting the division and/or proliferation (and in some cases, causing apoptosis) of a cancer cell, comprising administering an effective amount of a compound of the disclosure to a cell or subject in need thereof.

Cancer cells that can be treated with a compound of the disclosure may be any type of cancer including, but not limited to, hematopoietic malignancies, including leukemias, lymphomas, and myelomas as well as other types of cancer including sarcomas, carcinomas, melanomas, adenomas, nervous system cancers and genitourinary cancers. Examples of leukemias include acute lymphoblastic leukemia (ALL), acute myelocytic leukemia (AML), acute myelomonocytic leukemia (AMML), chronic myeloid leukemia (CML), chronic lymphocytic leukemia (CLL) and juvenile myelo-monocytic leukemia (JMML). In some embodiments, the compounds and compositions of this disclosure are useful in treating a cancer selected from, but not limited to, ovarian cancer, cervical cancer, brain cancer, lung cancer, skin cancer, colorectal cancer, esophageal cancer, breast cancer, prostate cancer, leukemia, multiple myeloma, bone cancer, pancreatic cancer, bladder cancer, endometrial cancer, kidney cancer, liver cancer, eye cancer, pituitary cancer, testicular cancer, and stomach cancer.

In addition to cancer, the compounds and the compositions of this disclosure are useful in treating a myelodysplastic syndrome (MDS) in a subject in need thereof, comprising administering an effective amount of a compound or composition of the disclosure to a cell or subject in need thereof. In some embodiments, compounds and compositions of Formula I are useful in treating MDS. In some embodiments, compounds and compositions of Formula II are useful in treating MDS. Myelodysplastic syndrome (MDS) refers to a diverse group of hematopoietic stem cell disorders. MDS is characterized by a cellular marrow with impaired morphology and maturation (dysmyelopoiesis), peripheral blood cytopenias, and a variable risk of progression to acute leukemia, resulting from ineffective blood cell production. *The Merck Manual* 953 (17$^{th}$ ed. 1999) and List et al., 1990, *J. Clin. Oncol.* 8:1424. In some embodiments, the compounds or compositions of this disclosure are useful in treating an MDS that is selected from, but not limited to, refractory anemia, refractory anemia with ringed sideroblasts, refractory anemia with excess blasts, refractory anemia with excess blasts in transformation and chronic myelomonocytic leukemia.

Furthermore, the compounds of the disclosure are useful in treating other conditions involving aberrant or abnormal cell proliferation. In some embodiments, compounds and compositions of Formula I are useful in treating conditions involving aberrant or abnormal cell proliferation. In some embodiments, compounds and compositions of Formula II are useful in treating conditions involving aberrant or abnormal cell proliferation. Other cell proliferative disorders that may be treated by the present invention include inflammatory diseases, allergies, autoimmune disease, graft rejection psoriasis, restenosis, atherosclerosis, and any other disorder wherein it is desirable to inhibit, prevent, or suppress cell growth. Compounds of the disclosure may be tested for their efficacy in a particular cell proliferation disorder using assays and techniques known to those of skill in the art.

Another aspect of this disclosure provides methods for treating a skin cancer in a subject in need thereof using a compound described herein. In some embodiments, compounds and compositions of Formula I are useful in treating MDS. In some embodiments, compounds and compositions of Formula II are useful in treating MDS. In some embodiments, the skin cancer that may be treated by a compound described herein is a melanoma. In some embodiments, the melanoma is selected from, but not limited to, lentigo maligna melanoma, superficial spreading melanoma, acral lentiginous melanoma, mucosal melanoma, nodular melanoma, polypoid melanoma, desmoplastic melanoma, amelanotic melanoma, soft-tissue melanoma, melanoma with small nevus-like cells, melanoma with features of a Spitz nevus, and uveal melanoma.

In addition to the above-mentioned therapeutic uses, the compounds of the disclosure are also useful in diagnostic assays, screening assays and as research tools.

In diagnostic assays, the compounds of the disclosure may be useful in identifying or detecting a cell proliferative disorder. In such an embodiment, the compounds of the disclosure may be radiolabelled (as hereinbefore described) and contacted with a population of cells. The presence of the radiolabel on the cells may indicate a cell proliferative disorder.

In screening assays, the compounds of the disclosure may be used to identify other compounds that destabilize microtubules, modulate cell division and/or proliferation. In such assays, the compounds may also be radiolabelled.

In another example, the compounds of this disclosure can be used to synthesize additional analogs and derivatives to improve their therapeutic activity (e.g., anticancer activity), including but not limited to improved stability, solubility, potency, specificity, bioavailability, efficacy, and delivery. In another example, the compounds of this disclosure can be used to synthesize additional analogs and derivatives to decrease their side effects, including but not limited to its toxicity or unwanted metabolites.

Compositions and Modes of Administration

In some embodiments (such as the uses described above), the compounds of the disclosure are formulated into pharmaceutical compositions for administration to subjects (such as human subjects) in a biologically compatible form suitable for administration in vivo. Accordingly, in another aspect, the present invention provides a pharmaceutical composition comprising a compound of the disclosure in admixture with a suitable diluent or carrier. Such a composition is useful for treating the conditions described herein.

The compositions containing the compounds of the disclosure can be prepared by known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the substances in association with one or more pharmaceutically acceptable vehicles or diluents, and contained in buffered solutions with a suitable pH and iso-osmotic with the physiological fluids.

The compounds of this invention may be used in treating the conditions described herein, in the form of the free base, salts (preferably pharmaceutically acceptable salts), solvates, hydrates, prodrugs, isomers, or mixtures thereof. All forms are within the scope of the disclosure. Acid addition salts may be formed and provide a more convenient form for use; in practice, use of the salt form inherently amounts to use of the base form. The acids which can be used to prepare the acid addition salts include preferably those which produce, when combined with the free base, pharmaceutically acceptable salts, that is, salts whose anions are non-toxic to the subject organism in pharmaceutical doses of the salts, so that the beneficial properties inherent in the free base are not vitiated by side effects ascribable to the anions. Although pharmaceutically acceptable salts of the basic compounds are preferred, all acid addition salts are useful as sources of the free base form even if the particular salt per se is desired only as an intermediate product as, for example, when the salt is formed only for the purposes of purification and identification, or when it is used as an intermediate in preparing a pharmaceutically acceptable salt by ion exchange procedures.

Pharmaceutically acceptable salts within the scope of the disclosure include those derived from the following acids; mineral acids such as hydrochloric acid, sulfuric acid, phosphoric acid and sulfamic acid; and organic acids such as acetic acid, citric acid, lactic acid, tartaric acid, malonic acid, methanesulfonic acid, ethanesulfonic acid, benzenesulfonic acid, p-toluenesulfonic acid, cyclohexylsulfamic acid, quinic acid, and the like.

In accordance with the methods of the disclosure, the described compounds may be administered to a patient in a variety of forms depending on the selected route of administration, as will be understood by those skilled in the art. The compositions of the disclosure may be administered orally or parenterally.

Parenteral administration includes intravenous, intraperitoneal, subcutaneous, intramuscular, transepithelial, nasal, intrapulmonary, intrathecal, rectal and topical modes of administration. Parenteral administration may be by continuous infusion over a selected period of time.

In certain embodiments, pharmaceutical compositions suitable for parenteral administration may comprise the compound of the present disclosure in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and non-aqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

A composition comprising a compound of the present disclosure may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

In certain embodiments of the disclosure, compositions comprising a compound of the present disclosure can be administered orally, e.g., in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and the like, each containing a predetermined amount of the compound of the present disclosure as an active ingredient.

In solid dosage forms for oral administration (capsules, tablets, pills, dragees, powders, granules, and the like), one or more compositions comprising the compound of the present disclosure may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration include pharmaceutically acceptable emulsions, microemulsions, solutions, suspensions, syrups, and elixirs. In addition to the compound of the present disclosure, the liquid dosage forms may contain inert diluents commonly used in the art, such as water or other solvents, solubilizing agents and emulsifiers, such as ethyl alcohol (ethanol), isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the active compounds, salts and/or prodrugs thereof, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

A person skilled in the art would know how to prepare suitable formulations. Conventional procedures and ingredients for the selection and preparation of suitable formulations are described, for example, in Remington's Pharmaceutical Sciences (1990—18th edition) and in The United States Pharmacopeia: The National Formulary (USP 24 NF19) published in 1999.

The pharmaceutical forms suitable for injectable use include sterile aqueous solutions or dispersion and sterile powders for the extemporaneous preparation of sterile injectable solutions or dispersions.

The compounds of the disclosure may be administered to a subject in need thereof alone or in combination with pharmaceutically acceptable carriers, as noted above, the proportion of which is determined by the solubility and chemical nature of the compound, chosen route of administration and standard pharmaceutical practice.

The dosage of the compounds and/or compositions of the disclosure can vary depending on many factors such as the pharmacodynamic properties of the compound, the mode of administration, the age, health and weight of the recipient, the nature and extent of the symptoms, the frequency of the treatment and the type of concurrent treatment, if any, and the clearance rate of the compound in the subject to be treated. One of skill in the art can determine the appropriate dosage based on the above factors. The compounds of the disclosure may be administered initially in a suitable dosage that may be adjusted as required, depending on the clinical response. To calculate the human equivalent dose (HED) from a dosage used in the treatment of age-dependent cognitive impairment in rats, the formula HED (mg/kg)=rat dose (mg/kg)×0.16 may be employed (see Estimating the Safe Starting Dose in Clinical Trials for Therapeutics in Adult Healthy Volunteers, December 2002, Center for Biologics Evaluation and Research). For example, using that formula, a dosage of 10 mg/kg in rats is equivalent to 1.6 mg/kg in humans. This conversion is based on a more general formula HED=animal dose in mg/kg×(animal weight in kg/human weight in kg)$^{0.33}$. Similarly, to calculate the HED from a dosage used in the treatment in mouse, the formula HED (mg/kg)=mouse dose (mg/kg)×0.08 may be employed (see Estimating the Safe Starting Dose in Clinical Trials for Therapeutics in Adult Healthy Volunteers, December 2002, Center for Biologics Evaluation and Research).

The compounds of the disclosure can be used alone or conjointly with other therapeutic agents, or in combination with other types of treatment (which may or may not modulate stability of microtubules) for treating cell proliferative disorders. For example, these other therapeutically useful agents may be administered in a single formulation, simultaneously or sequentially with the compound of the present disclosure according to the methods of the disclosure.

There are various examples of other types of treatment for cell proliferative disorders currently used to treat different types of cancers. In a particular aspect of the present invention, the compounds of the disclosure may be used in combination with other therapies and therapeutics to treat leukemia.

In some embodiments, the method of treating or preventing cancer, such as those described above, may comprise administering a compound or composition of the disclosure conjointly with one or more other chemotherapeutic agent (s). Chemotherapeutic agents that may be conjointly administered with compounds or compositions of the disclosure include: aminoglutethimide, amsacrine, anastrozole, asparaginase, bcg, bicalutamide, bleomycin, bortezomib, buserelin, busulfan, campothecin, capecitabine, carboplatin, carfilzomib, carmustine, chlorambucil, chloroquine, cisplatin, cladribine, clodronate, colchicine, cyclophosphamide, cyproterone, cytarabine, dacarbazine, dactinomycin, daunorubicin, demethoxyviridin, dichloroacetate, dienestrol, diethylstilbestrol, docetaxel, doxorubicin, epirubicin, estradiol, estramustine, etoposide, everolimus, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, lenalidomide, letrozole, leucovorin, leuprolide, levamisole, lomustine, lonidamine, mechlorethamine, medroxyprogesterone, megestrol, melphalan, mercaptopurine, mesna, metformin, methotrexate, mitomycin, mitotane, mitoxantrone, nilutamide, nocodazole, octreotide, oxaliplatin, paclitaxel, pamidronate, pentostatin, perifosine, plicamycin, pomalidomide, porfimer, procarbazine, raltitrexed, rituximab, sorafenib, streptozocin, sunitinib, suramin, tamoxifen, temozolomide, temsirolimus, teniposide, testosterone, thalidomide, thioguanine, thiotepa, titanocene dichloride, topotecan, trastuzumab, tretinoin, vinblastine, vincristine, vindesine, and vinorelbine. In certain embodiments of the methods of the disclosure described herein, the chemotherapeutic agent conjointly administered with compounds of the disclosure is a taxane chemotherapeutic agent, such as paclitaxel or docetaxel. In certain embodiments of the methods of the disclosure described herein, the chemotherapeutic agent conjointly administered with compounds of the disclosure is doxorubicin. In certain embodiments of the methods of the disclosure described herein, a compound of the disclosure is administered conjointly with a taxane chemotherapeutic agent (e.g., paclitaxel) and doxorubicin.

Many combination therapies have been developed for the treatment of cancer. In certain embodiments, compounds or compositions of the disclosure may be conjointly administered with a combination therapy. Examples of combination therapies with which compounds of the disclosure may be conjointly administered are included in Table 1.

TABLE 1

Exemplary combinatorial therapies for the treatment of cancer.

| Name | Therapeutic agents |
|---|---|
| ABV | Doxorubicin, Bleomycin, Vinblastine |
| ABVD | Doxorubicin, Bleomycin, Vinblastine, Dacarbazine |

TABLE 1-continued

Exemplary combinatorial therapies for the treatment of cancer.

| Name | Therapeutic agents |
|---|---|
| AC (Breast) | Doxorubicin, Cyclophosphamide |
| AC (Sarcoma) | Doxorubicin, Cisplatin |
| AC (Neuroblastoma) | Cyclophosphamide, Doxorubicin |
| ACE | Cyclophosphamide, Doxorubicin, Etoposide |
| ACe | Cyclophosphamide, Doxorubicin |
| AD | Doxorubicin, Dacarbazine |
| AP | Doxorubicin, Cisplatin |
| ARAC-DNR | Cytarabine, Daunorubicin |
| B-CAVe | Bleomycin, Lomustine, Doxorubicin, Vinblastine |
| BCVPP | Carmustine, Cyclophosphamide, Vinblastine, Procarbazine, Prednisone |
| BEACOPP | Bleomycin, Etoposide, Doxorubicin, Cyclophosphamide, Vincristine, Procarbazine, Prednisone, Filgrastim |
| BEP | Bleomycin, Etoposide, Cisplatin |
| BIP | Bleomycin, Cisplatin, Ifosfamide, Mesna |
| BOMP | Bleomycin, Vincristine, Cisplatin, Mitomycin |
| CA | Cytarabine, Asparaginase |
| CABO | Cisplatin, Methotrexate, Bleomycin, Vincristine |
| CAF | Cyclophosphamide, Doxorubicin, Fluorouracil |
| CAL-G | Cyclophosphamide, Daunorubicin, Vincristine, Prednisone, Asparaginase |
| CAMP | Cyclophosphamide, Doxorubicin, Methotrexate, Procarbazine |
| CAP | Cyclophosphamide, Doxorubicin, Cisplatin |
| CaT | Carboplatin, Paclitaxel |
| CAV | Cyclophosphamide, Doxorubicin, Vincristine |
| CAVE ADD | CAV and Etoposide |
| CA-VP16 | Cyclophosphamide, Doxorubicin, Etoposide |
| CC | Cyclophosphamide, Carboplatin |
| CDDP/VP-16 | Cisplatin, Etoposide |
| CEF | Cyclophosphamide, Epirubicin, Fluorouracil |
| CEPP(B) | Cyclophosphamide, Etoposide, Prednisone, with or without/Bleomycin |
| CEV | Cyclophosphamide, Etoposide, Vincristine |
| CF | Cisplatin, Fluorouracil or Carboplatin Fluorouracil |
| CHAP | Cyclophosphamide or Cyclophosphamide, Altretamine, Doxorubicin, Cisplatin |
| ChlVPP | Chlorambucil, Vinblastine, Procarbazine, Prednisone |
| CHOP | Cyclophosphamide, Doxorubicin, Vincristine, Prednisone |
| CHOP-BLEO | Add Bleomycin to CHOP |
| CISCA | Cyclophosphamide, Doxorubicin, Cisplatin |
| CLD-BOMP | Bleomycin, Cisplatin, Vincristine, Mitomycin |
| CMF | Methotrexate, Fluorouracil, Cyclophosphamide |
| CMFP | Cyclophosphamide, Methotrexate, Fluorouracil, Prednisone |
| CMFVP | Cyclophosphamide, Methotrexate, Fluorouracil, Vincristine, Prednisone |
| CMV | Cisplatin, Methotrexate, Vinblastine |
| CNF | Cyclophosphamide, Mitoxantrone, Fluorouracil |
| CNOP | Cyclophosphamide, Mitoxantrone, Vincristine, Prednisone |
| COB | Cisplatin, Vincristine, Bleomycin |
| CODE | Cisplatin, Vincristine, Doxorubicin, Etoposide |
| COMLA | Cyclophosphamide, Vincristine, Methotrexate, Leucovorin, Cytarabine |
| COMP | Cyclophosphamide, Vincristine, Methotrexate, Prednisone |
| Cooper Regimen | Cyclophosphamide, Methotrexate, Fluorouracil, Vincristine, Prednisone |
| COP | Cyclophosphamide, Vincristine, Prednisone |
| COPE | Cyclophosphamide, Vincristine, Cisplatin, Etoposide |
| COPP | Cyclophosphamide, Vincristine, Procarbazine, Prednisone |
| CP(Chronic lymphocytic leukemia) | Chlorambucil, Prednisone |
| CP (Ovarian Cancer) | Cyclophosphamide, Cisplatin |
| CT | Cisplatin, Paclitaxel |
| CVD | Cisplatin, Vinblastine, Dacarbazine |
| CVI | Carboplatin, Etoposide, Ifosfamide, Mesna |
| CVP | Cyclophosphamide, Vincristine, Prednisone |
| CVPP | Lomustine, Procarbazine, Prednisone |
| CYVADIC | Cyclophosphamide, Vincristine, Doxorubicin, Dacarbazine |
| DA | Daunorubicin, Cytarabine |
| DAT | Daunorubicin, Cytarabine, Thioguanine |
| DAV | Daunorubicin, Cytarabine, Etoposide |
| DCT | Daunorubicin, Cytarabine, Thioguanine |
| DHAP | Cisplatin, Cytarabine, Dexamethasone |
| DI | Doxorubicin, Ifosfamide |

TABLE 1-continued

Exemplary combinatorial therapies for the treatment of cancer.

| Name | Therapeutic agents |
|---|---|
| DTIC/Tamoxifen | Dacarbazine, Tamoxifen |
| DVP | Daunorubicin, Vincristine, Prednisone |
| EAP | Etoposide, Doxorubicin, Cisplatin |
| EC | Etoposide, Carboplatin |
| EFP | Etoposie, Fluorouracil, Cisplatin |
| ELF | Etoposide, Leucovorin, Fluorouracil |
| EMA 86 | Mitoxantrone, Etoposide, Cytarabine |
| EP | Etoposide, Cisplatin |
| EVA | Etoposide, Vinblastine |
| FAC | Fluorouracil, Doxorubicin, Cyclophosphamide |
| FAM | Fluorouracil, Doxorubicin, Mitomycin |
| FAMTX | Methotrexate, Leucovorin, Doxorubicin |
| FAP | Fluorouracil, Doxorubicin, Cisplatin |
| F-CL | Fluorouracil, Leucovorin |
| FEC | Fluorouracil, Cyclophosphamide, Epirubicin |
| FED | Fluorouracil, Etoposide, Cisplatin |
| FL | Flutamide, Leuprolide |
| FZ | Flutamide, Goserelin acetate implant |
| HDMTX | Methotrexate, Leucovorin |
| Hexa-CAF | Altretamine, Cyclophosphamide, Methotrexate, Fluorouracil |
| ICE-T | Ifosfamide, Carboplatin, Etoposide, Paclitaxel, Mesna |
| IDMTX/6-MP | Methotrexate, Mercaptopurine, Leucovorin |
| IE | Ifosfamide, Etoposide, Mesna |
| IfoVP | Ifosfamide, Etoposide, Mesna |
| IPA | Ifosfamide, Cisplatin, Doxorubicin |
| M-2 | Vincristine, Carmustine, Cyclophosphamide, Prednisone, Melphalan |
| MAC-III | Methotrexate, Leucovorin, Dactinomycin, Cyclophosphamide |
| MACC | Methotrexate, Doxorubicin, Cyclophosphamide, Lomustine |
| MACOP-B | Methotrexate, Leucovorin, Doxorubicin, Cyclophosphamide, Vincristine, Bleomycin, Prednisone |
| MAID | Mesna, Doxorubicin, Ifosfamide, Dacarbazine |
| m-BACOD | Bleomycin, Doxorubicin, Cyclophosphamide, Vincristine, Dexamethasone, Methotrexate, Leucovorin |
| MBC | Methotrexate, Bleomycin, Cisplatin |
| MC | Mitoxantrone, Cytarabine |
| MF | Methotrexate, Fluorouracil, Leucovorin |
| MICE | Ifosfamide, Carboplatin, Etoposide, Mesna |
| MINE | Mesna, Ifosfamide, Mitoxantrone, Etoposide |
| mini-BEAM | Carmustine, Etoposide, Cytarabine, Melphalan |
| MOBP | Bleomycin, Vincristine, Cisplatin, Mitomycin |
| MOP | Mechlorethamine, Vincristine, Procarbazine |
| MOPP | Mechlorethamine, Vincristine, Procarbazine, Prednisone |
| MOPP/ABV | Mechlorethamine, Vincristine, Procarbazine, Prednisone, Doxorubicin, Bleomycin, Vinblastine |
| MP (multiple myeloma) | Melphalan, Prednisone |
| MP (prostate cancer) | Mitoxantrone, Prednisone |
| MTX/6-MO | Methotrexate, Mercaptopurine |
| MTX/6-MP/VP | Methotrexate, Mercaptopurine, Vincristine, Prednisone |
| MTX-CDDPAdr | Methotrexate, Leucovorin, Cisplatin, Doxorubicin |
| MV (breast cancer) | Mitomycin, Vinblastine |
| MV (acute myelocytic leukemia) | Mitoxantrone, Etoposide |
| M-VAC Methotrexate | Vinblastine, Doxorubicin, Cisplatin |
| MVP Mitomycin | Vinblastine, Cisplatin |
| MVPP | Mechlorethamine, Vinblastine, Procarbazine, Prednisone |
| NFL | Mitoxantrone, Fluorouracil, Leucovorin |
| NOVP | Mitoxantrone, Vinblastine, Vincristine |
| OPA | Vincristine, Prednisone, Doxorubicin |
| OPPA | Add Procarbazine to OPA. |
| PAC | Cisplatin, Doxorubicin |
| PAC-I | Cisplatin, Doxorubicin, Cyclophosphamide |
| PA-CI | Cisplatin, Doxorubicin |
| PC | Paclitaxel, Carboplatin or Paclitaxel, Cisplatin |
| PCV | Lomustine, Procarbazine, Vincristine |
| PE | Paclitaxel, Estramustine |
| PFL | Cisplatin, Fluorouracil, Leucovorin |
| POC | Prednisone, Vincristine, Lomustine |
| ProMACE | Prednisone, Methotrexate, Leucovorin, Doxorubicin, Cyclophosphamide, Etoposide |
| ProMACE/cytaBOM | Prednisone, Doxorubicin, Cyclophosphamide, Etoposide, Cytarabine, Bleomycin, Vincristine, Methotrexate, |

TABLE 1-continued

Exemplary combinatorial therapies for the treatment of cancer.

| Name | Therapeutic agents |
|---|---|
| | Leucovorin, Cotrimoxazole |
| PRoMACE/MOPP | Prednisone, Doxorubicin, Cyclophosphamide, Etoposide, Mechlorethamine, Vincristine, Procarbazine, Methotrexate, Leucovorin |
| Pt/VM | Cisplatin, Teniposide |
| PVA | Prednisone, Vincristine, Asparaginase |
| PVB | Cisplatin, Vinblastine, Bleomycin |
| PVDA | Prednisone, Vincristine, Daunorubicin, Asparaginase |
| SMF | Streptozocin, Mitomycin, Fluorouracil |
| TAD | Mechlorethamine, Doxorubicin, Vinblastine, Vincristine, Bleomycin, Etoposide, Prednisone |
| TCF | Paclitaxel, Cisplatin, Fluorouracil |
| TIP | Paclitaxel, Ifosfamide, Mesna, Cisplatin |
| TTT | Methotrexate, Cytarabine, Hydrocortisone |
| Topo/CTX | Cyclophosphamide, Topotecan, Mesna |
| VAB-6 | Cyclophosphamide, Dactinomycin, Vinblastine, Cisplatin, Bleomycin |
| VAC | Vincristine, Dactinomycin, Cyclophosphamide |
| VACAdr | Vincristine, Cyclophosphamide, Doxorubicin, Dactinomycin, Vincristine |
| VAD | Vincristine, Doxorubicin, Dexamethasone |
| VATH | Vinblastine, Doxorubicin, Thiotepa, Flouxymesterone |
| VBAP | Vincristine, Carmustine, Doxorubicin, Prednisone |
| VBCMP | Vincristine, Carmustine, Melphalan, Cyclophosphamide, Prednisone |
| VC | Vinorelbine, Cisplatin |
| VCAP | Vincristine, Cyclophosphamide, Doxorubicin, Prednisone |
| VD | Vinorelbine, Doxorubicin |
| VelP | Vinblastine, Cisplatin, Ifosfamide, Mesna |
| VIP | Etoposide, Cisplatin, Ifosfamide, Mesna |
| VM | Mitomycin, Vinblastine |
| VMCP | Vincristine, Melphalan, Cyclophosphamide, Prednisone |
| VP | Etoposide, Cisplatin |
| V-TAD | Etoposide, Thioguanine, Daunorubicin, Cytarabine |
| 5 + 2 | Cytarabine, Daunorubicin, Mitoxantrone |
| 7 + 3 | Cytarabine with/, Daunorubicin or Idarubicin or Mitoxantrone |
| "8 in 1" | Methylprednisolone, Vincristine, Lomustine, Procarbazine, Hydroxyurea, Cisplatin, Cytarabine, Dacarbazine |

In certain embodiments, a compound or composition of the disclosure may be conjointly administered with non-chemical methods of cancer treatment. In certain embodiments, a compound or composition of the disclosure may be conjointly administered with radiation therapy. In certain embodiments, a compound or composition of the disclosure may be conjointly administered with surgery, with thermoablation, with focused ultrasound therapy, with cryotherapy, or with any combination of these.

In certain embodiments, different compounds of the disclosure may be conjointly administered with one or more other compounds of the disclosure. Moreover, such combinations may be conjointly administered with other therapeutic agents, such as other agents suitable for the treatment of cancer, such as the agents identified above.

It will be understood by one of ordinary skill in the art that the compositions and methods described herein may be adapted and modified as is appropriate for the application being addressed and that the compositions and methods described herein may be employed in other suitable applications, and that such other additions and modifications will not depart from the scope hereof. For example, in addition to the therapeutic uses described herein, the compounds and compositions of this disclosure can be used as research tools or chemical probes to, for example, understand normal cell or cancer cell biological processes, including but not limited to microtubule dynamics, cell division, cell proliferation, and the types of cells that are resistant or sensitive to the compounds or compositions of this disclosure. The disclosure contemplates all uses of the compounds and compositions of the disclosure, including their use in therapeutic methods and compositions for modulating cell division, their use in diagnostic assays and their use as research tools.

Definitions

Unless otherwise defined herein, scientific and technical terms used in this application shall have the meanings that are commonly understood by those of ordinary skill in the art. Generally, nomenclature used in connection with, and techniques of, chemistry, cell and tissue culture, molecular biology, cell and cancer biology, neurobiology, neurochemistry, virology, immunology, microbiology, pharmacology, genetics and protein and nucleic acid chemistry, described herein, are those well known and commonly used in the art.

The methods and techniques of the present disclosure are generally performed, unless otherwise indicated, according to conventional methods well known in the art and as described in various general and more specific references that are cited and discussed throughout this specification. See, e.g. "Principles of Neural Science", McGraw-Hill Medical, New York, N.Y. (2000); Motulsky, "Intuitive Biostatistics", Oxford University Press, Inc. (1995); Lodish et al., "Molecular Cell Biology, 4th ed.", W. H. Freeman &

Co., New York (2000); Griffiths et al., "Introduction to Genetic Analysis, 7th ed.", W. H. Freeman & Co., N.Y. (1999); and Gilbert et al., "Developmental Biology, 6th ed.", Sinauer Associates, Inc., Sunderland, M A (2000).

Chemistry terms used herein are used according to conventional usage in the art, as exemplified by "The McGraw-Hill Dictionary of Chemical Terms", Parker S., Ed., McGraw-Hill, San Francisco, Calif. (1985).

All of the above, and any other publications, patents and published patent applications referred to in this application are specifically incorporated by reference herein. In case of conflict, the present specification, including its specific definitions, will control.

The term "agent" is used herein to denote a chemical compound (such as an organic or inorganic compound, a mixture of chemical compounds), a biological macromolecule (such as a nucleic acid, an antibody, including parts thereof as well as humanized, chimeric and human antibodies and monoclonal antibodies, a protein or portion thereof, e.g., a peptide, a lipid, a carbohydrate), or an extract made from biological materials such as bacteria, plants, fungi, or animal (particularly mammalian) cells or tissues. Agents include, for example, agents whose structure is known, and those whose structure is not known. The microtubule-stabilizing or -destabilizing activity of such agents may render them suitable as "therapeutic agents" in the methods and compositions of this disclosure.

A "patient," "subject," or "individual" are used interchangeably and refer to either a human or a non-human animal. These terms include mammals, such as humans, primates, livestock animals (including bovines, porcines, etc.), companion animals (e.g., canines, felines, etc.) and rodents (e.g., mice and rats).

"Treating" a condition or patient refers to taking steps to obtain beneficial or desired results, including clinical results. As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount.

"Administering" or "administration of" a substance, a compound or an agent to a subject can be carried out using one of a variety of methods known to those skilled in the art. For example, a compound or an agent can be administered, intravenously, arterially, intradermally, intramuscularly, intraperitoneally, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods.

Appropriate methods of administering a substance, a compound or an agent to a subject will also depend, for example, on the age and/or the physical condition of the subject and the chemical and biological properties of the compound or agent (e.g. solubility, digestibility, bioavailability, stability and toxicity). In some embodiments, a compound or an agent is administered orally, e.g., to a subject by ingestion. In some embodiments, the orally administered compound or agent is in an extended release or slow release formulation, or administered using a device for such slow or extended release.

As used herein, the phrase "conjoint administration" refers to any form of administration of two or more different therapeutic agents such that the second agent is administered while the previously administered therapeutic agent is still effective in the body (e.g., the two agents are simultaneously effective in the patient, which may include synergistic effects of the two agents). For example, the different therapeutic compounds can be administered either in the same formulation or in separate formulations, either concomitantly or sequentially. Thus, an individual who receives such treatment can benefit from a combined effect of different therapeutic agents.

A "therapeutically effective amount" or a "therapeutically effective dose" of a drug or agent is an amount of a drug or an agent that, when administered to a subject will have the intended therapeutic effect. The full therapeutic effect does not necessarily occur by administration of one dose, and may occur only after administration of a series of doses. Thus, a therapeutically effective amount may be administered in one or more administrations. The precise effective amount needed for a subject will depend upon, for example, the subject's size, health and age, and the nature and extent of the condition being treated, such as cancer or MDS. The skilled worker can readily determine the effective amount for a given situation by routine experimentation.

The term "antimitotic agent(s)" or "antimitotic(s)", as used herein, means a compound (or compounds) that inhibits cell growth by interfering with cell division. Antimitotic agents include antimicrotubule agents, mitotic inhibitors, and/or taxanes. Docetaxel and paclitaxel are exemplary antimitotic agents. Antimitotic agents that interact with tubulin protein are of interest because of their potential uses in the treatment of human neoplastic and inflammatory diseases. In some embodiments of the present disclosure, the compounds as described herein target the microtubules. Important dynamics of the microtubule polymers include their growth rate at the plus ends, catastrophic shortening, frequency of transition between the two phases, pause between the two phases, their release from the microtubule organizing center, and treadmilling (Margolis and Wilson, 1981; Mitchison and Kirschner, 1984; Kirschner and Mitchison, 1986; Margolis and Wilson, 1998; Jordan and Wilson, 2004). In some embodiments, the compounds of this disclosure disrupt the normal microtubule dynamics by acting on (or affecting) one or more of the above aspects of the microtubule dynamics.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkyl" refers to saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_{1-30}$ for straight chains, $C_{3-30}$ for branched chains), and more preferably 20 or fewer.

Moreover, the term "alkyl" as used throughout the specification, examples, and claims is intended to include both unsubstituted and substituted alkyl groups, the latter of which refers to alkyl moieties having substituents replacing a hydrogen on one or more carbons of the hydrocarbon backbone, including haloalkyl groups such as trifluoromethyl and 2,2,2-trifluoroethyl, etc.

The term "$C_{x-y}$" or "Cx-Cy", when used in conjunction with a chemical moiety, such as, acyl, acyloxy, alkyl, alkenyl, alkynyl, or alkoxy is meant to include groups that contain from x to y carbons in the chain. $C_0$alkyl indicates a hydrogen where the group is in a terminal position, a bond if internal. A $C_{1-6}$alkyl group, for example, contains from one to six carbon atoms in the chain.

The term "alkylamino", as used herein, refers to an amino group substituted with at least one alkyl group.

The term "alkylthio", as used herein, refers to a thiol group substituted with an alkyl group and may be represented by the general formula alkylS—.

The term "amide", as used herein, refers to a group

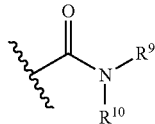

wherein $R^9$ and $R^{10}$ each independently represent a hydrogen or hydrocarbyl group, or $R^9$ and $R^{10}$ taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

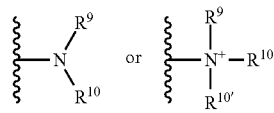

wherein $R^9$, $R^{10}$, and $R^{10'}$ each independently represent a hydrogen or a hydrocarbyl group, or $R^9$ and $R^{10}$ taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

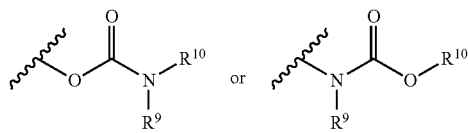

wherein $R^9$ and $R^{10}$ independently represent hydrogen or a hydrocarbyl group.

The term "carbocyclylalkyl", as used herein, refers to an alkyl group substituted with a carbocycle group.

The terms "carbocycle", "carbocyclyl", and "carbocyclic", as used herein, refers to a non-aromatic saturated or unsaturated ring in which each atom of the ring is carbon. Preferably a carbocycle ring contains from 3 to 10 atoms, more preferably from 5 to 7 atoms.

The term "carbocyclylalkyl", as used herein, refers to an alkyl group substituted with a carbocycle group.

The term "carbonate" is art-recognized and refers to a group —$OCO_2$—.

The term "carboxy", as used herein, refers to a group represented by the formula —$CO_2H$.

The term "ester", as used herein, refers to a group —$C(O)OR^9$ wherein $R^9$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The term "heterocyclylalkyl", as used herein, refers to an alkyl group substituted with a heterocycle group.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and even trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "sulfate" is art-recognized and refers to the group —OSO$_3$H, or a pharmaceutically acceptable salt thereof.

The term "sulfonamide" is art-recognized and refers to the group represented by the general formulae

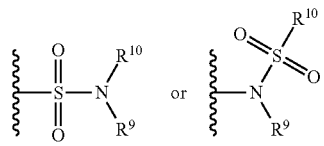

wherein $R^9$ and $R^{10}$ independently represents hydrogen or hydrocarbyl.

The term "sulfoxide" is art-recognized and refers to the group—S(O)—.

The term "sulfonate" is art-recognized and refers to the group SO$_3$H, or a pharmaceutically acceptable salt thereof.

The term "sulfone" is art-recognized and refers to the group —S(O)$_2$—.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

The term "thioalkyl", as used herein, refers to an alkyl group substituted with a thiol group.

The term "thioester", as used herein, refers to a group —C(O)SR$^9$ or —SC(O)R$^9$ wherein R$^9$ represents a hydrocarbyl.

The term "thioether", as used herein, is equivalent to an ether, wherein the oxygen is replaced with a sulfur.

The term "urea" is art-recognized and may be represented by the general formula

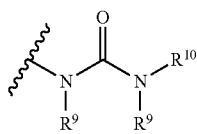

wherein $R^9$ and $R^{10}$ independently represent hydrogen or a hydrocarbyl.

The term "modulate" as used herein includes the inhibition or suppression of a function or activity (such as cell proliferation) as well as the enhancement of a function or activity.

The phrase "pharmaceutically acceptable" is art-recognized. In certain embodiments, the term includes compositions, excipients, adjuvants, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable salt" or "salt" is used herein to refer to an acid addition salt or a basic addition salt which is suitable for or compatible with the treatment of patients.

The term "pharmaceutically acceptable acid addition salt" as used herein means any non-toxic organic or inorganic salt of any base compounds represented by Formula I. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts of compounds of Formula I are more soluble in water and various hydrophilic organic solvents, and generally demonstrate higher melting points in comparison to their free base forms. The selection of the appropriate salt will be known to one skilled in the art. Other non-pharmaceutically acceptable salts, e.g., oxalates, may be used, for example, in the isolation of compounds of Formula I for laboratory use, or for subsequent conversion to a pharmaceutically acceptable acid addition salt.

The term "pharmaceutically acceptable basic addition salt" as used herein means any non-toxic organic or inorganic base addition salt of any acid compounds represented by Formula I or any of their intermediates. Illustrative inorganic bases which form suitable salts include lithium, sodium, potassium, calcium, magnesium, or barium hydroxide. Illustrative organic bases which form suitable salts include aliphatic, alicyclic, or aromatic organic amines such as methylamine, trimethylamine and picoline or ammonia. The selection of the appropriate salt will be known to a person skilled in the art.

Many of the compounds useful in the methods and compositions of this disclosure have at least one stereogenic center in their structure. This stereogenic center may be present in a R or a S configuration, said R and S notation is used in correspondence with the rules described in Pure Appl. Chem. (1976), 45, 11-30. The disclosure contemplates all stereoisomeric forms such as enantiomeric and diastereoisomeric forms of the compounds, salts, prodrugs or mixtures thereof (including all possible mixtures of stereoisomers). See, e.g., WO 01/062726.

Furthermore, certain compounds which contain alkenyl groups may exist as Z (zusammen) or E (entgegen) isomers. In each instance, the disclosure includes both mixture and separate individual isomers.

Some of the compounds may also exist in tautomeric forms. Such forms, although not explicitly indicated in the formulae described herein, are intended to be included within the scope of the present disclosure.

"Prodrug" or "pharmaceutically acceptable prodrug" refers to a compound that is metabolized, for example hydrolyzed or oxidized, in the host after administration to form the compound of the present disclosure (e.g., compounds of formula I). Typical examples of prodrugs include compounds that have biologically labile or cleavable (protecting) groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, or dephosphorylated to produce the active compound. Examples of prodrugs using ester or phosphoramidate as biologically labile or cleavable (protecting) groups are disclosed in U.S. Pat. Nos. 6,875,751, 7,585,851, and 7,964,580, the disclosures of which are incorporated herein by reference. The prodrugs of this disclosure are metabolized to produce a compound of Formula I. The present disclosure includes within its scope, prodrugs of the compounds described herein. Conventional procedures for the selection and preparation of suitable prodrugs are described, for example, in "Design of Prodrugs" Ed. H. Bundgaard, Elsevier, 1985.

The phrase "pharmaceutically acceptable carrier" as used herein means a pharmaceutically acceptable material, composition or vehicle, such as a liquid or solid filter, diluent, excipient, solvent or encapsulating material useful for formulating a drug for medicinal or therapeutic use.

The term "myelodysplastic syndrome" or "MDS" means a hematopoietic stem cell disorder characterized by one or more of the following: ineffective blood cell production, progressive cytopenias, risk of progression to acute leukemia or cellular marrow with impaired morphology and maturation (dysmyelopoiesis). The term "myelodysplastic syndrome" or "MDS" includes, but is not limited to, refractory anemia, refractory anemia with ringed sideroblasts, refractory anemia with excess blasts, refractory anemia with excess blasts in transformation and chronic myelomonocytic leukemia.

The term "Log of solubility", "Log S" or "log S" as used herein is used in the art to quantify the aqueous solubility of a compound. The aqueous solubility of a compound significantly affects its absorption and distribution characteristics. A low solubility often goes along with a poor absorption. Log S value is a unit stripped logarithm (base 10) of the solubility measured in mol/liter.

This disclosure will be better understood from the Experimental Details which follow. However, one skilled in the art will readily appreciate that the specific methods and results discussed are merely illustrative of the disclosure as described more fully in the embodiments which follow thereafter.

EXEMPLIFICATION

Example 1 Synthetic Protocols

Chemistry: General Experimental Procedures. All reagents and solvents were purchased from commercial suppliers and used without further purification unless otherwise stated. The reactions were monitored by thin layer chromatography (TLC) on precoated silica gel F254 plates (Sigma-Aldrich) with a UV indicator using chloroform:methanol (9.5:0.5 v/v). Yields were of purified product and were not optimized. The purity of the newly synthesized compounds was determined by LCMS analysis. The proton nuclear resonance (1H NMR) spectra were performed on a Varian GEMINI 2000 NMR spectrometer system with working frequency 400 MHz. Chemical shifts (δ) are given in ppm, and the following abbreviations are used: singlet (s), doublet (d), triplet (t), quartet (q), multiplet (m), and broad singlet (br s). All LCMS data were gathered on an Agilent 1100 LC system. The compound solution was injected into the ionization source (APCI) operating positive and negative modes with a mobile phase acetonitrile/water/formic acid (50:50:0.1% v/v) at 1.0 mL/min. The instrument was externally calibrated for the mass range m/z 100 to m/z 650.

Certain compounds of the invention were synthesized according to Scheme 2 and as outlined in the following general procedures.

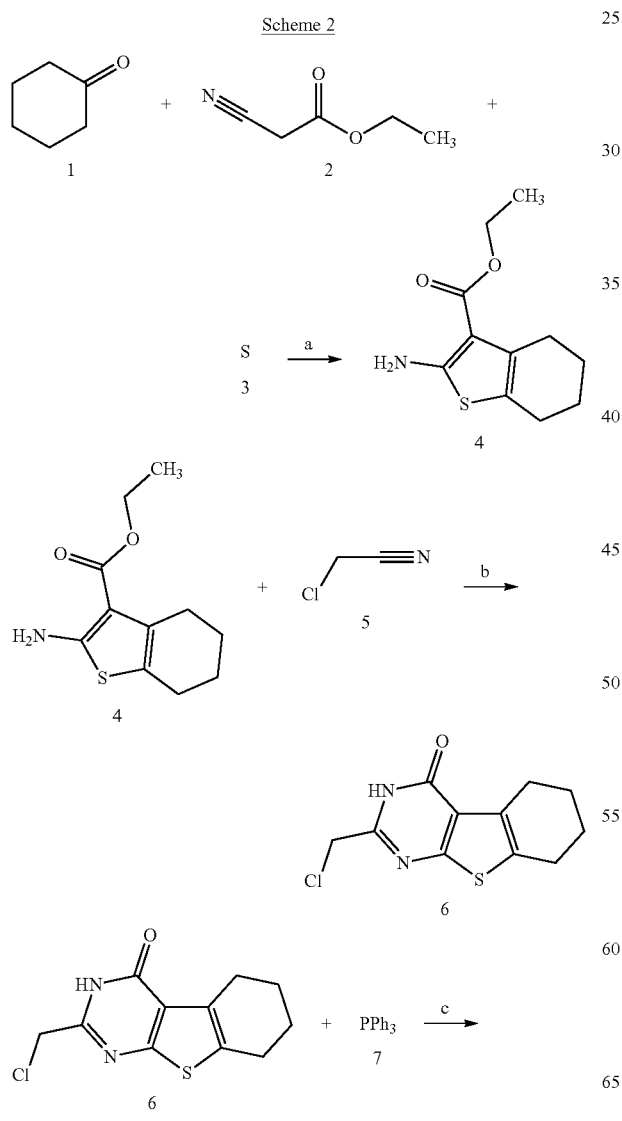

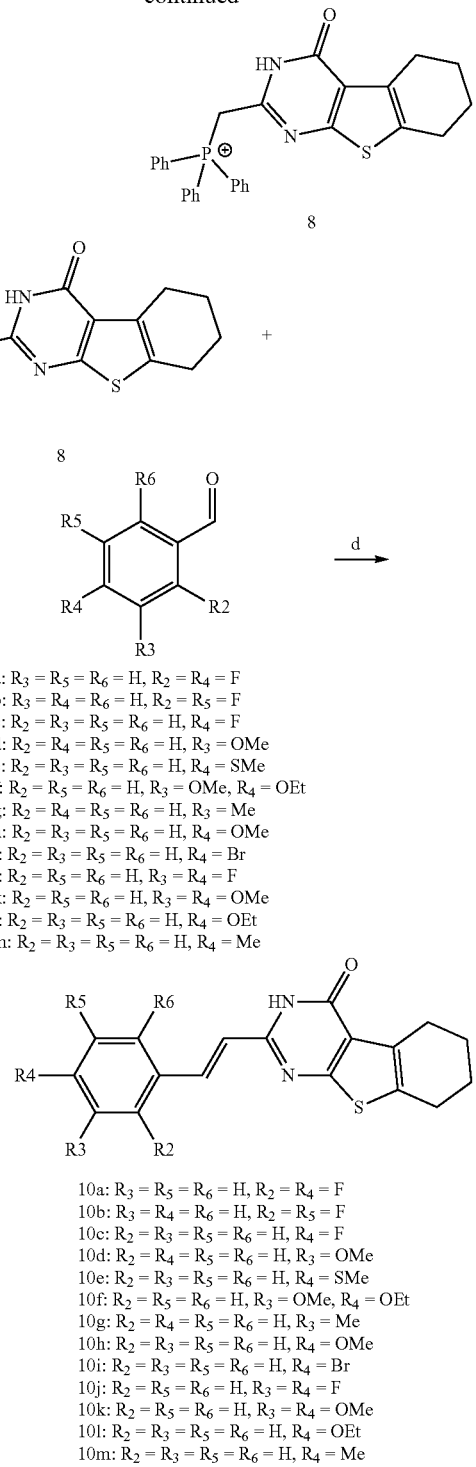

9a: $R_3 = R_5 = R_6 = H, R_2 = R_4 = F$
9b: $R_3 = R_4 = R_6 = H, R_2 = R_5 = F$
9c: $R_2 = R_3 = R_5 = R_6 = H, R_4 = F$
9d: $R_2 = R_4 = R_5 = R_6 = H, R_3 = OMe$
9e: $R_2 = R_3 = R_5 = R_6 = H, R_4 = SMe$
9f: $R_2 = R_5 = R_6 = H, R_3 = OMe, R_4 = OEt$
9g: $R_2 = R_4 = R_5 = R_6 = H, R_3 = Me$
9h: $R_2 = R_3 = R_5 = R_6 = H, R_4 = OMe$
9i: $R_2 = R_3 = R_5 = R_6 = H, R_4 = Br$
9j: $R_2 = R_5 = R_6 = H, R_3 = R_4 = F$
9k: $R_2 = R_5 = R_6 = H, R_3 = R_4 = OMe$
9l: $R_2 = R_3 = R_5 = R_6 = H, R_4 = OEt$
9m: $R_2 = R_3 = R_5 = R_6 = H, R_4 = Me$

10a: $R_3 = R_5 = R_6 = H, R_2 = R_4 = F$
10b: $R_3 = R_4 = R_6 = H, R_2 = R_5 = F$
10c: $R_2 = R_3 = R_5 = R_6 = H, R_4 = F$
10d: $R_2 = R_4 = R_5 = R_6 = H, R_3 = OMe$
10e: $R_2 = R_3 = R_5 = R_6 = H, R_4 = SMe$
10f: $R_2 = R_5 = R_6 = H, R_3 = OMe, R_4 = OEt$
10g: $R_2 = R_4 = R_5 = R_6 = H, R_3 = Me$
10h: $R_2 = R_3 = R_5 = R_6 = H, R_4 = OMe$
10i: $R_2 = R_3 = R_5 = R_6 = H, R_4 = Br$
10j: $R_2 = R_5 = R_6 = H, R_3 = R_4 = F$
10k: $R_2 = R_5 = R_6 = H, R_3 = R_4 = OMe$
10l: $R_2 = R_3 = R_5 = R_6 = H, R_4 = OEt$
10m: $R_2 = R_3 = R_5 = R_6 = H, R_4 = Me$

Reagents and conditions: (a) Morpholine (20.4 g, 0.234 mol), EtOH, 50 C; (b) HCl, 3 hr, 1,4-dioxane, 50 C; (c) toluene, 8 hr; (d) Na2CO3 (0.8 mL, 10%), MeOH, rt.

General Procedure for the Preparation of Ethyl-2-amino-4,5,6,7-tetrahydrobenzo[b]thiophene-3-carboxylate. (Intermediate 4)

Morpholine (20.4 g, 0.234 mol) was added dropwise to a mixture of cyclohexanone (10.0 g, 0.102 mol), ethyl cyanoacetate (11.53 g, 0.102 mol), and sulfur (2.9 g, 0.094 mol) in 30 mL of ethanol at ambient temperature in 20 min. The reaction was exothermic, so the temperature increased to 50° C., and a clear solution was obtained. It was filtered from solids and cooled to 0-5° C. After stirring for 1 h the product was filtered off, washed with chilled ethanol (15 mL) and sucked dry. The obtained cake was dried in an oven at 50° C. for 3 h to obtain 14 g of the title product. Yield: 66.0%. 1H NMR (ppm): 1.23 (3H, t), 1.61-1.72 (4H, m), 2.38-2.41 (2H, m), 2.56-2.61 (2H, m), 4.13 (2H, d), 7.21 (2H, br.s).

General Procedure for the Preparation of 2-(Chloromethyl)-5,6,7,8-tetrahydrobenzo[4,5]thieno[2,3-d]pyrimidin-4(3H)-one. (Intermediate 6)

Ethyl 2 amino 4,5,6,7 tetrahydrobenzothiophene-3-carboxylate (11.25 g, 0.05 mol) and chloroacetonitrile (5.0 g, 0.06 mol) were dissolved 1,4-dioxane. The obtained solution was heated to 50° C., and passed with dry hydrogen chloride gas for 3 h until the starting material disappeared. Then the solvent was removed under vacuum. The residue was triturated with hexane, and a precipitate was formed as a fine powder. The product was filtered, washed with hexane, and air dried to obtain 8.1 g of the compound. Yield: 63.0%. 1H NMR (ppm): 1.71-1.82 (4H, m), 2.74 (2H, d.tr), 2.87 (2H, d.tr), 4.53 (2H, s), 12.5 (1H, br.s).

General Procedure for the Preparation of ((4-Oxo-3,4,5,6,7,8-hexahydrobenzo[4,5]thieno[2,3-d]pyrimidin-2-yl)methyl) triphenylphosphonium chloride. (Intermediate 8)

0.01 mol of compound 6 and 0.01 mol of thriphenylphosphine were boiled in 50 mL of toluene for 10 h. The resulting residue was filtered off, washed with toluene, air dried and used for condensation with aldehydes without further purification. Yield: 75%. 1H NMR (ppm): 1.60-1.80 (4H, m), 12.90 (1H, br.s), 2.65 (2H, d.tr), 2.77 (2H, d.tr), 8.60 (2H, d), 8.70-8.80 (6H, m), 8.80-8.90 (9H, m).

General Procedure for the Preparation of Compound 10 and its Analogs 10a-10m

A 10% solution of $Na_2CO_3$ (0.8 mL) was added dropwise to a solution of thriphenylphosphonium chloride 8 (0.001 mol) and corresponding aldehyde 9 (0.0005 mol) in methanol. The reaction mixture was stirred for 10 min at RT. The resulting yellow precipitate was filtered off, washed with water and methanol. The remaining residue was boiled in ethanol for 2 h, filtered hot, washed with alcohol and dried to give the final compound as a solid.

(E)-2-styryl-5,6,7,8-tetrahydrobenzo[4,5]thieno[2,3-d]pyrimidin-4(3H)-one (Compound 10). Yield: 46%. Purity 95% by LCMS. 1H NMR (ppm): 1.70-1.82 (4H, m), 2.75 (2H, d.t), 2.59 (2H, d.t), 6.98 (1H, d), 7.39-7.51 (3H, m), 7.68-7.81 (2H, m), 7.98 (1H, d), 12.97 (1H, br.s).

(E)-2-(2,4-difluorostyryl)-5,6,7,8-tetrahydrobenzo[4,5]thieno[2,3-d]pyrimidin-4(3H)-one (Compound 10a). Yield: 40%. Purity 95% by LCMS. 1H NMR (DMSO-d6, 400 MHz): δ 1.76-1.86 (4H, m), 2.75 (2H, d.t), 2.88 (2H, d.t), 7.03 (1H, d), 7.18-7.22 (1H, m), 7.34-7.41 (1H, m), 7.76-7.82 (1H, m), 7.86 (1H, d), 12.42 (1H, br.s).

(E)-2-(2,5-difluorostyryl)-5,6,7,8-tetrahydrobenzo[4,5]thieno[2,3-d]pyrimidin-4(3H)-one (Compound 10b). Yield: 42%. Purity 98% by LCMS. 1H NMR (DMSO-d6, 400 MHz): δ 1.76-1.86 (4H, m), 2.75 (2H, d.t), 2.89 (2H, d.t), 7.12 (1H, d), 7.27-7.40 (2H, m), 7.59-7.62 (1H, m), 7.86 (1H, d), 12.45 (1H, br.s).

(E)-2-(4-fluorostyryl)-5,6,7,8-tetrahydrobenzo[4,5]thieno[2,3-d]pyrimidin-4(3H)-one (Compound 10c). Yield: 33%. Purity 97% by LCMS. 1H NMR (DMSO-d6, 400 MHz): δ 1.76-1.86 (4H, m), 2.75 (2H, d.t), 2.89 (2H, d.t), 6.92 (1H, d), 7.24-7.32 (2H, m), 7.65-7.73 (2H, m), 7.87 (1H, d), 12.30 (1H, br.s).

(E)-2-(3-methoxystyryl)-5,6,7,8-tetrahydrobenzo[4,5]thieno[2,3-d]pyrimidin-4(3H)-one (Compound 10d). Yield: 36%. Purity 98% by LCMS. 1H NMR (DMSO-d6, 400 MHz): δ 1.75-1.88 (4H, m), 2.75 (2H, d.t), 2.88 (2H, d.t), 3.80 (3H, s) 6.98 (1H, d), 6.99 (1H, dd), 7.20 (1H, d), 7.21 (1H, d), 7.36 (1H, t), 7.84 (1H, d), 12.30 (1H, br.).

(E)-2-(4-methylthiostyryl)-5,6,7,8-tetrahydrobenzo[4,5]thieno[2,3-d]pyrimidin-4(3H)-one (Compound 10e). Yield: 39%. Purity 95% by LCMS. 1H NMR (DMSO-d6, 400 MHz): δ 1.76-1.86 (4H, m), 2.52 (3H, s), 2.76 (2H, d.t), 2.91 (2H, d.t), 6.92 (1H, d), 7.32 (2H, d), 7.55 (2H, d), 7.84 (1H, d), 11.95 (1H, br.s).

(E)-2-(4-ethoxy-3-methoxystyryl)-5,6,7,8-tetrahydrobenzo[4,5]thieno[2,3-d]pyrimidin-4(3H)-one (Compound 10f). Yield: 46%. Purity 96% by LCMS. 1H NMR (DMSO-d6, 400 MHz): δ 1.34 (3H, t), 1.76-1.86 (4H, m), 2.75 (2H, d.t), 2.89 (2H, d.t), 3.82 (3H, s), 4.06 (2H, q), 6.86 (1H, d), 7.00 (1H, d), 7.16 (1H, dd), 7.24 (1H, d), 7.82 (1H, d), 12.20 (1H, br.s).

(E)-2-(3-methylstyryl)-5,6,7,8-tetrahydrobenzo[4,5]thieno[2,3-d]pyrimidin-4(3H)-one (Compound 10g). Yield: 56%. Purity 95% by LCMS. 1H NMR (DMSO-d6, 400 MHz): δ 1.76-1.86 (4H, m), 2.36 (3H, s), 2.76 (2H, d.t), 2.91 (2H, d.t), 6.96 (1H, d), 7.22 (1H, dd), 7.33 (1H, t), 7.42 (1H, d), 7.43 (1H, d), 7.83 (1H, d), 12.15 (1H, br.s).

(E)-2-(4-methoxystyryl)-5,6,7,8-tetrahydrobenzo[4,5]thieno[2,3-d]pyrimidin-4(3H)-one (Compound 10h). Yield: 55%. Purity 95% by LCMS. 1H NMR (DMSO-d6, 400 MHz): δ 1.75-1.88 (4H, m), 2.74 (2H, d.t), 2.88 (2H, d.t), 3.80 (3H, s) 6.83 (1H, d), 7.01 (2H, d), 7.58 (2H, d), 7.83 (1H, d), 12.24 (1H, br.s).

(E)-2-(4-bromostyryl)-5,6,7,8-tetrahydrobenzo[4,5]thieno[2,3-d]pyrimidin-4(3H)-one (Compound 10i). Yield: 39%. Purity 96% by LCMS. 1H NMR (DMSO-d6, 400 MHz): δ 1.75-1.88 (4H, m), 2.75 (2H, d.t), 2.88 (2H, d.t), 6.98 (1H, d), 7.58 (2H, d), 7.64 (2H, d), 7.83 (1H, d), 12.34 (1H, br.s).

(E)-2-(3,4-difluorostyryl)-5,6,7,8-tetrahydrobenzo[4,5]thieno[2,3-d]pyrimidin-4(3H)-one (10j). Yield: 53%. Purity 95% by LCMS. 1H NMR (DMSO-d6, 400 MHz): δ 1.76-1.90 (4H, m), 2.76 (2H, d.t), 2.90 (2H, d.t), 6.95 (1H, d), 7.44-7.52 (2H, m), 7.64-7.71 (1H, m), 7.82 (1H, d), 12.10 (1H, br.s).

(E)-2-(3,4-dimethoxystyryl)-5,6,7,8-tetrahydrobenzo[4,5]thieno[2,3-d]pyrimidin-4(3H)-one (Compound 10k). Yield: 30%. Purity 95% by LCMS. 1H NMR (DMSO-d6, 400 MHz): δ 1.76-1.86 (4H, m), 2.75 (2H, d.t), 2.89 (2H, d.t), 3.80 (3H, s), 3.81 (3H, s), 6.86 (1H, d), 7.02 (1H, d), 7.19 (1H, dd), 7.24 (1H, d), 7.82 (1H, d), 12.45 (1H, br.s).

(E)-2-(4-ethoxystyryl)-5,6,7,8-tetrahydrobenzo[4,5]thieno[2,3-d]pyrimidin-4(3H)-one (10l). Yield: 52%. Purity 95% by LCMS. 1H NMR (DMSO-d6, 400 MHz): δ 1.36 (3H, t), 1.76-1.86 (4H, m), 2.75 (2H, d.t), 2.89 (2H, d.t), 4.11 (2H, q), 6.82 (1H, d), 6.99 (2H, d), 7.55 (2H, d), 7.81 (1H, d), 11.90 (1H, br.s).

(E)-2-(4-methylstyryl)-5,6,7,8-tetrahydrobenzo[4,5]thieno[2,3-d]pyrimidin-4(3H)-one (Compound 10m). Yield: 41%. Purity 95% by LCMS. 1H NMR (DMSO-d6, 400

MHz): δ 1.76-1.86 (4H, m), 2.35 (3H, s), 2.76 (2H, d.t), 2.91 (2H, d.t), 6.92 (1H, d), 7.25 (2H, d), 7.52 (2H, d), 7.83 (1H, d), 12.05 (1H, br.s).

Compounds 10n-10z are commercially available from MolPort (Latvia) and were found to be >95% purity by LCMS.

Example 2: Structure-Activity Relationship Studies for Certain Compounds of the Invention The cell viability $IC_{50}$ of each compound was determined using Promega CellTiter-Glo Luminescent Cell Viability Assay kit by measuring the total ATP levels to quantify the number of metabolically active cells upon drug treatment as described in Crouch et al., *J Immunol Methods* 1993, 160, (1), 81-8. Briefly, the compounds were suspended in DMSO at 10 mM and diluted in 384 plates (20 μl/well in DMSO) in triplicate by a 14-point titration (12 nM to 100 μM). 50 μl of HeLa cells or patient derived glioblastoma cells (HK-309) (2000 cells/well) were then treated with the prepared dilutions of the drugs (0.5 μl) and incubated at 37° C. and 5% $CO_2$. 72 hours later 50 μl of CellTiter-Glo reagent was added to each well followed by a 2 minutes shaking and a 10-minute incubation to lyse the cells. The relative luminescent intensity units (RLU) of each well was measured using a Tecan M1000 microplate reader (Tecan Group Ltd.) with its green filter and 1 second integration time.

The SAR data for certain compounds of the invention is summarized in Table 2.

Cells used in Example 2 and other examples disclosed herein were cultured as follows: Adherent HeLa cells and patient derived glioblastoma cells were grown with 5% $CO_2$ at 37° C. in F12:DMEM 50:50 medium (Invitrogen) containing 10% FBS and 1% penicillin/streptomycin. To obtain HeLa cells synchronized in mitosis, cycling cells were treated with 2 mM thymidine (Sigma-Aldrich) for eighteen hours, washed three times with PBS, and released into fresh media until they entered mitosis eight hours post-release. Patient-derived glioblastoma cells (HK-309) were collected and grown with approval from the UCLA Institutional Review Board. HK-309 was derived from a recurrent glioblastoma taken from a 55 year old male. The cells were initially propagated as cancer stem cell-containing spheres in serum-free medium containing basic fibroblast growth factor and epidermal growth factor (Preprotech) as described previously by Visnyei et al., *Mol Cancer Ther* 2011, 10, (10), 1818-28.

TABLE 2

Cell Viability IC50 Values for CSI Compounds Tested in HeLa Cells

| Compound | R1 | R2 | R3 | $IC_{50}$ [μM] |
|---|---|---|---|---|
| 10 | H | H | H | 0.552 |
| 10a | 2,4-F | H | H | 0.246 |
| 10b | 2,5-F | H | H | 0.159 |
| 10c | 4-F | H | H | 1.11 |
| 10d | 3-$OCH_3$ | H | H | 4.21 |
| 10e | 4-$SCH_3$ | H | H | 6.31 |
| 10f | 3-$OCH_3$,4-$OCH_2CH_3$ | H | H | 25.9 |
| 10g | 3-$CH_3$ | H | H | >100 |
| 10h | 4-$OCH_3$ | H | H | 50.9 |
| 10i | 4-Br | H | H | >100 |
| 10j | 3,4-F | H | H | >100 |
| 10k | 3,4-$OCH_3$ | H | H | >100 |
| 10l | 4-$OCH_2CH_3$ | H | H | >100 |
| 10m | 4-$CH_3$ | H | H | >100 |
| 10n | 4-$OCF_2$ | CN | 3-$CH_3$ | >100 |
| 10o | 2-$OCF_2$ | CN | 3-$CH_3$ | >100 |
| 10p | 2,5-$CH_3$ | CN | 3-$CH_3$ | >100 |
| 10q | 4-$CF_3$ | CN | H | >100 |
| 10r | 2,6-Cl | CN | 3-$CH_3$ | >100 |
| 10s | 3,4-Cl | H | H, decane ring | >100 |
| 10t | 3-$CH_3$ | CN | 3-$CH_3$ | >100 |
| 10u | 2-$CF_3$ | H | H | >100 |
| 10v | 4-$CH_2CH_3$ | CN | 3-$CH_3$ | >100 |
| 10w | 2-$CH_3$ | CN | 3-$CH_3$ | >100 |
| 10x | 2,4,6-$CH_3$ | CN | H | >100 |
| 10y | 2-$CF_3$ | CN | H | >100 |
| 10z | 2,4,6-$CH_3$ | CN | 3-$CH_3$ | >100 |

Example 3: Microtubule Polymerization Assays

Figure 2:
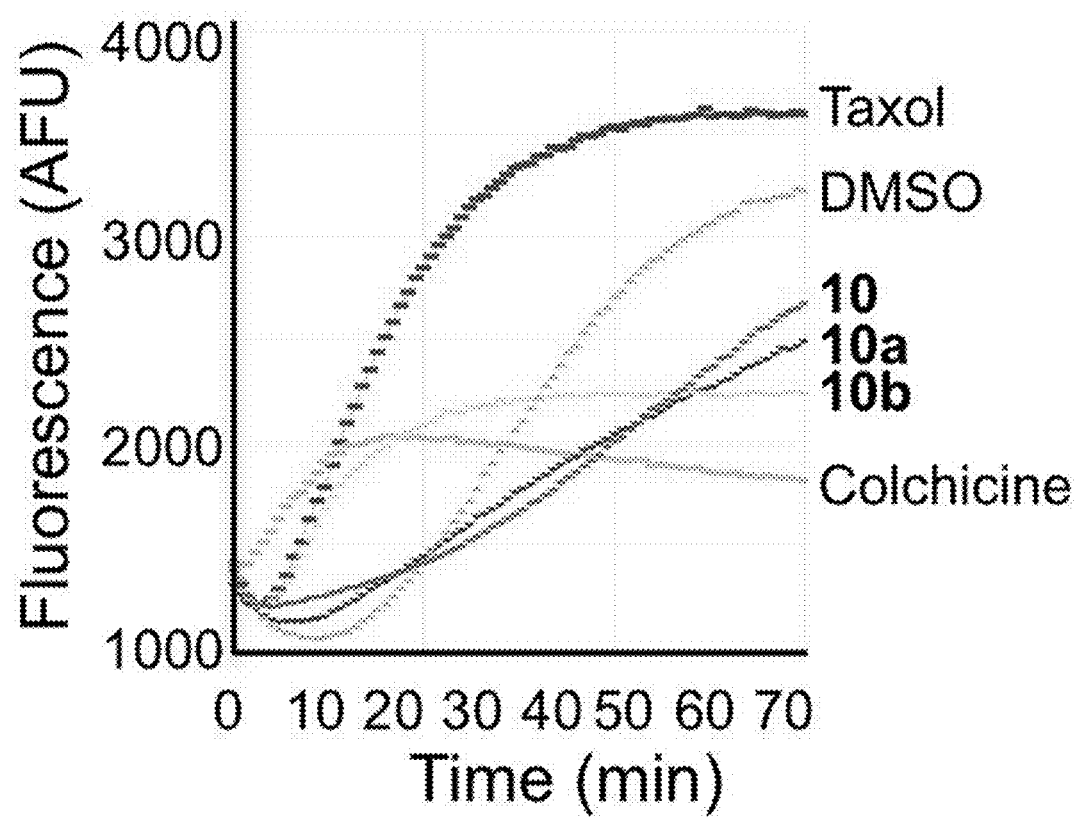
FIG. 2 shows the in vitro microtubule polymerization inhibition after treatment with DMSO, 3 μM taxol, 3 μM colchicine or 3 μM of Compounds 10, 10a, or 10b.
Figure 6A:
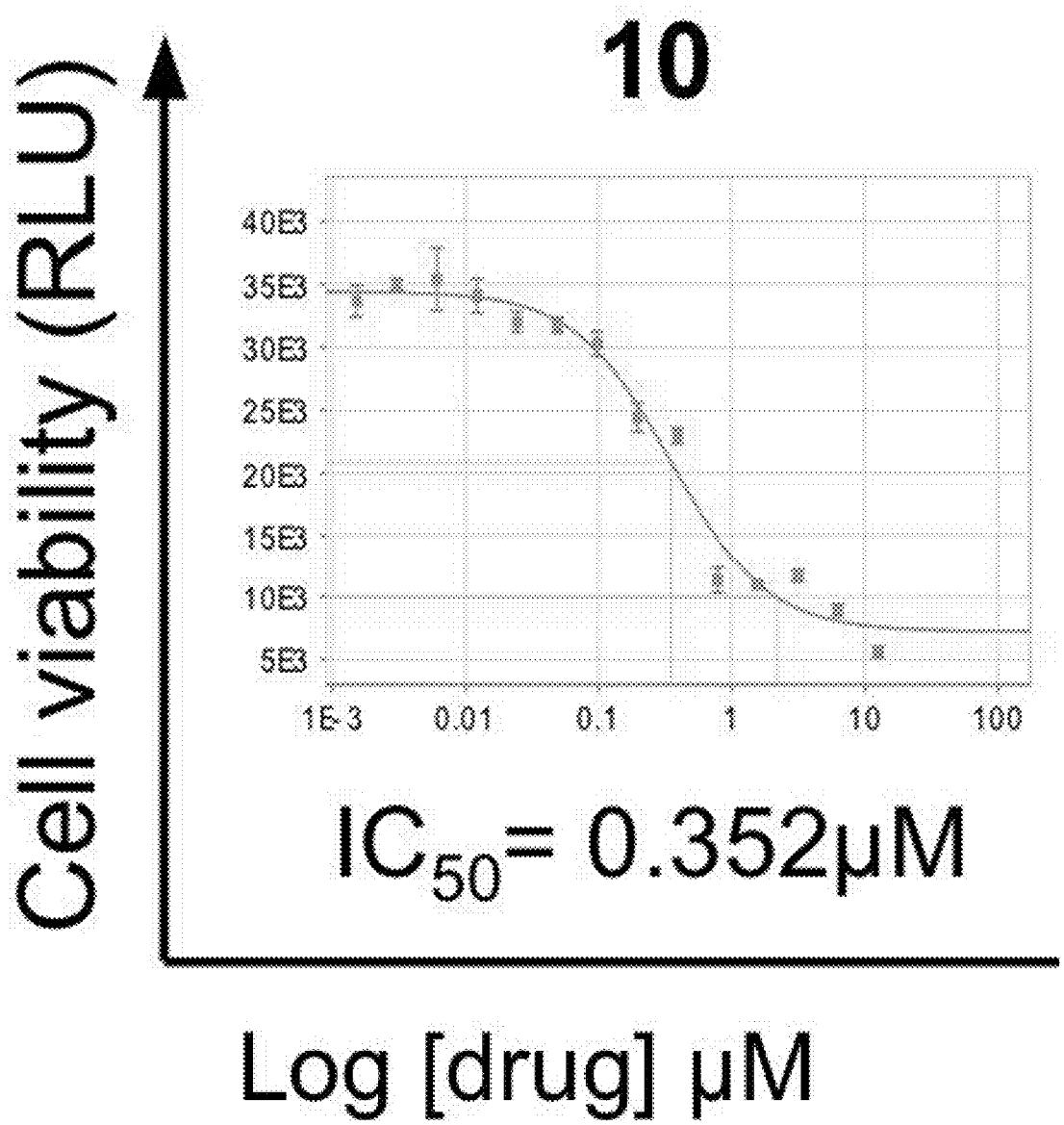
FIG. 6A shows the cell viability IC$_{50}$ for patient-derived glioblastoma cells treated with compound 10.
Figure 6B:
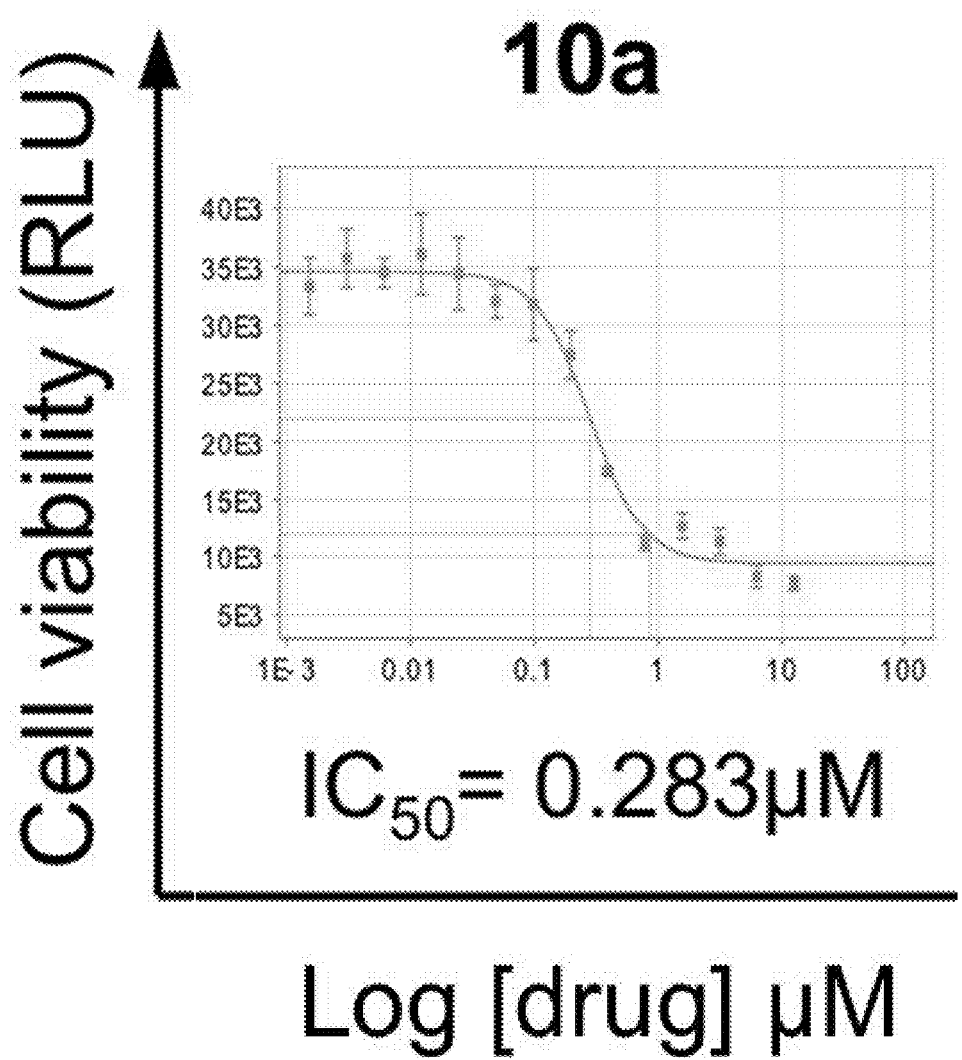

To further validate that compound 10 and its analogues were targeting microtubules, in vitro microtubule polymerization reactions were performed with the most potent compounds (10-10b) using the HTS-tubulin polymerization assay kit from Cytoskeleton Inc. Briefly, tubulin polymerization assays were conducted using the HTS-Tubulin polymerization assay kit from Cytoskeleton Inc. The reactions were carried out according to the manufacturer instructions (Cytoskeleton, BK011P) in the presence of 3 μM of test compounds (10, 10a, and 10b) and controls (DMSO, colchicine and taxol). 1.5 ul of 10× strength compound, 20 μl of tubulin solution and Triton X-100 at a final concentration of 0.01% were added to each well in a 384 well plate. The reactions were assembled on ice to prevent tubulin pre-polymerization. For kinetic measurements, microtubule polymerization was monitored by reading the fluorescence at 420 nm (due to the incorporation of a fluorescent reporter into microtubules as polymerization occurs) every ten seconds using a Tecan M1000 microplate reader (FIG. 6B). Both endpoint and kinetic measurements indicated that in vitro 10, 10a and 10b were potent inhibitors of microtubule polymerization similar to colchicine (FIG. 6A, B). For kinetic measurements, microtubule polymerization was monitored by reading the fluorescence at 420 nm (due to the incorporation of a fluorescent reporter into microtubules as polymerization occurs) every ten seconds using a Tecan M1000 microplate reader (FIG. 6B). Fluorescence increased as polymerization occurred, due to the incorporation of 4',6-diamidino-2-phenylindole. Fluorescence was monitored every minute for 70 minutes at 37° C. See FIG. 2. Both endpoint and kinetic measurements indicated that in vitro 10, 10a and 10b were potent inhibitors of microtubule polymerization similar to colchicine.

Next, microtubule stability was analyzed in HeLa cells treated with increasing concentrations of each of these three compounds by fixing the cells with 4% paraformaldehyde, staining them with Hoechst 33342 (DNA dye) to visualize their DNA and anti-α-tubulin antibodies to visualize microtubule structures and then imaging them by immunofluorescence microscopy. This analysis showed that, similar to colchicine, the microtubules of 10, 10a and 10b-treated cells became destabilized in a drug dose-dependent manner.

Example 4: Cell Cycle Analysis

Figure 1B:
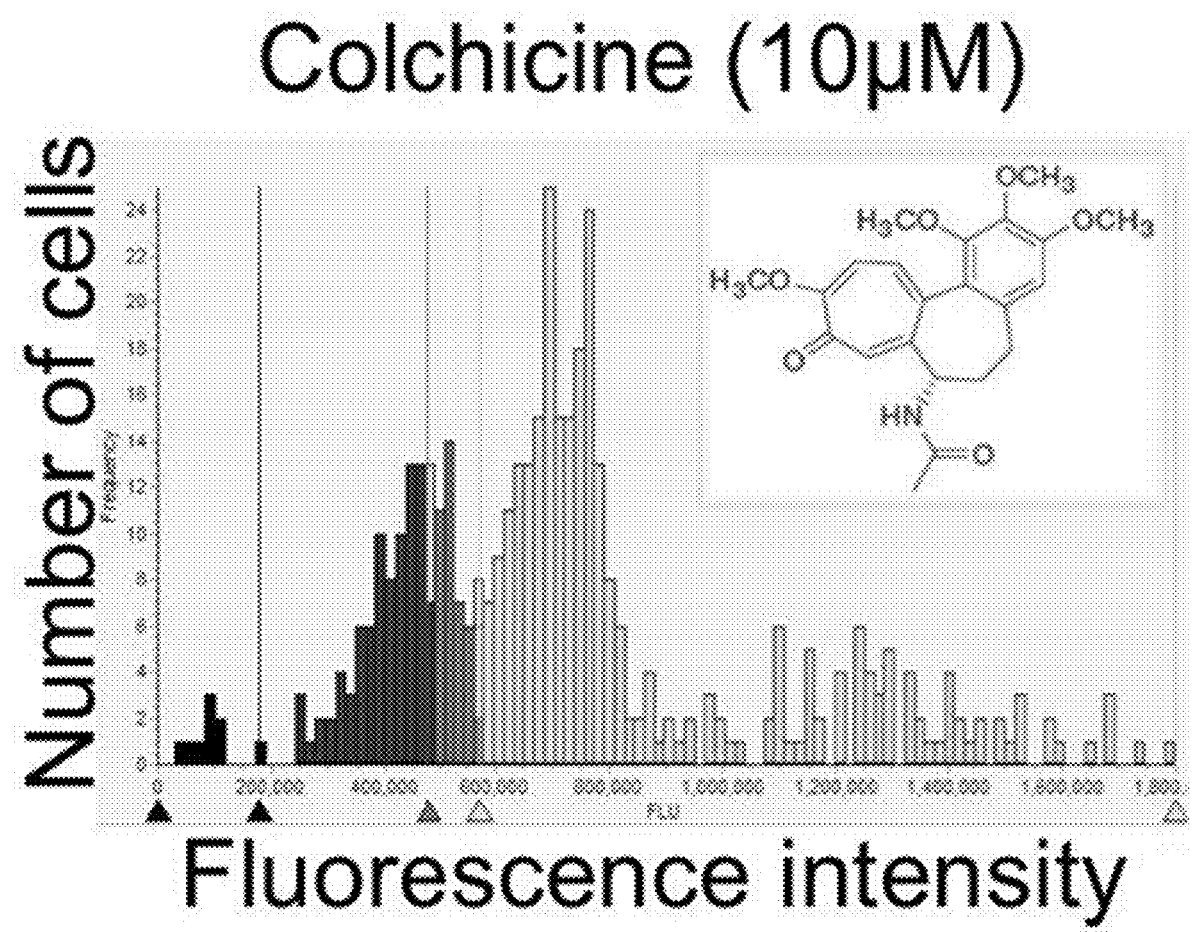
FIG. 1B shows that the cell cycle histogram of HeLa cells treated with 10 μM of colchicine for 20 hours. The percentage of cells in G1 phase, S phase and G2/M phase is indicated below the histogram for each treatment.
Figure 1C:
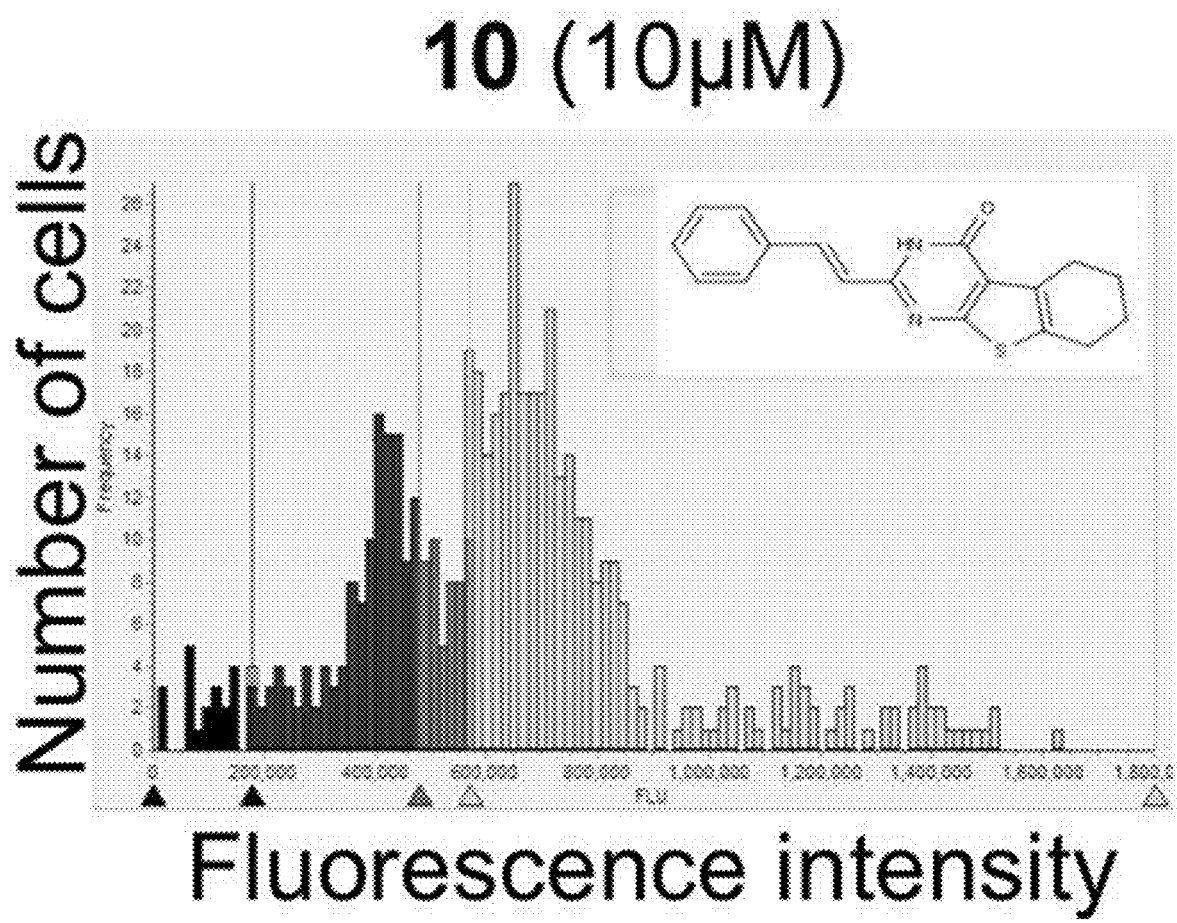
FIG. 1C shows that the cell cycle histogram of HeLa cells treated with 10 μM of compound 10 for 20 hours. The percentage of cells in G1 phase, S phase and G2/M phase is indicated below the histogram for each treatment.
Figure 3:
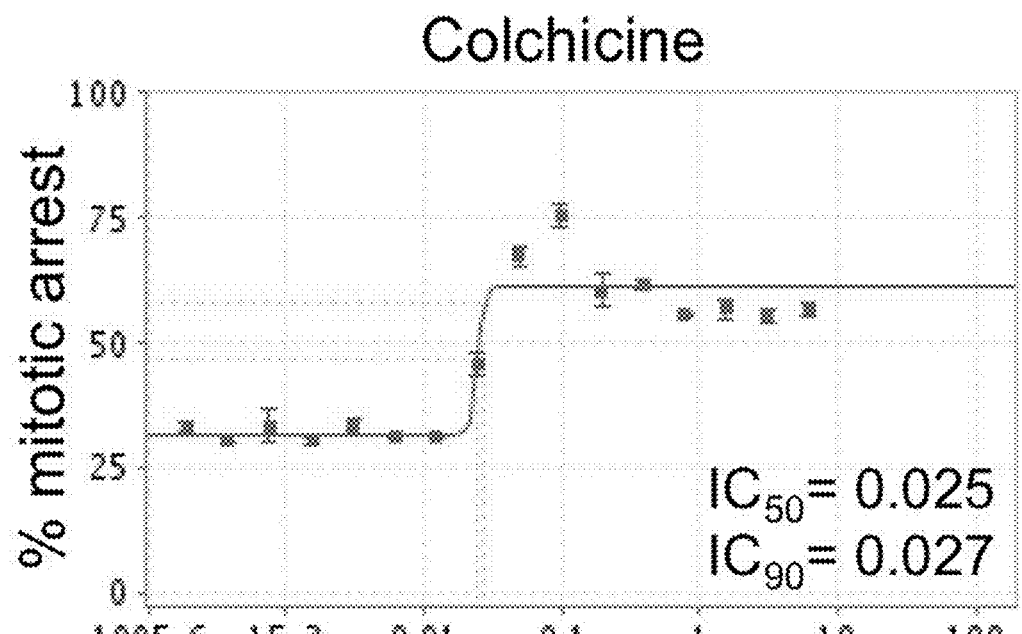
FIG. 3 shows the drug response dose curves to measure mitotic arrest $IC_{50}$s for increasing treatment with colchicine and compound 10.
Figure 3:
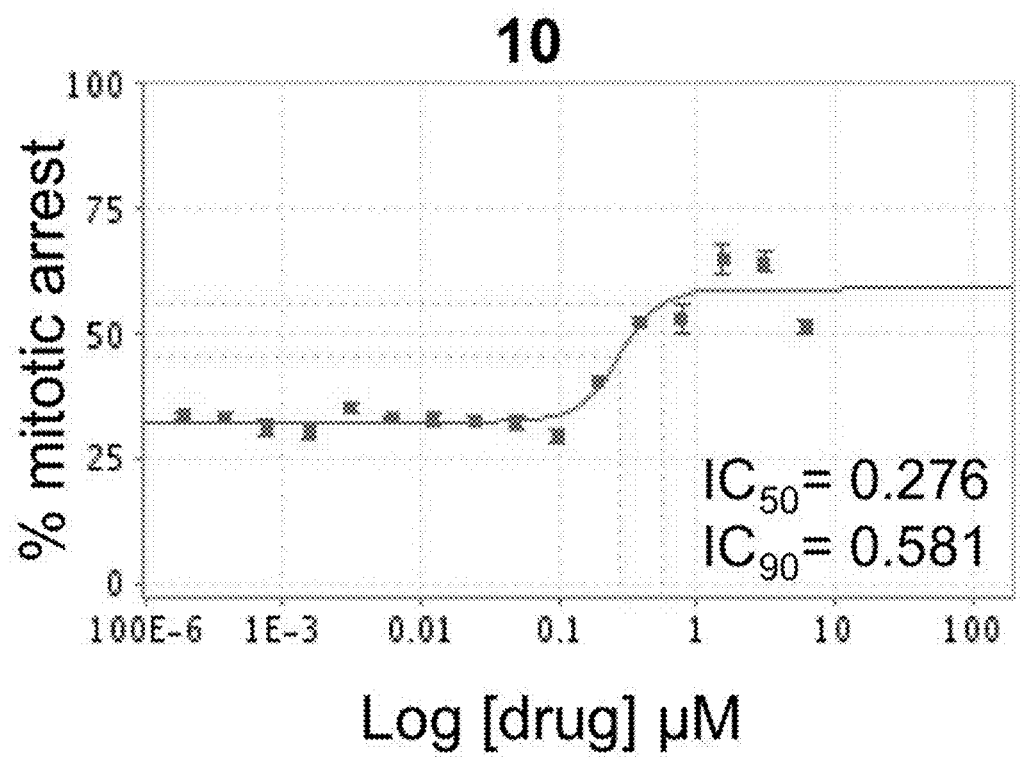

For cell cycle analysis, HeLa cells were plated in 384 well plates (1500 cells/well) and treated with 10 µM drugs for 20 hours. Cells were then fixed and stained with 5 µM Vybrant DyeCycle Green (Invitrogen) for 1 hour at 37° C. and plates were scanned with an Acumen eX3 (TTP Labtech) fluorescence microplate cytometer using its 488 nm laser and a cell cycle histogram profile was generated for each drug treatment using the CDD (Collaborative Drug Discovery) software. FIGS. 1A-C shows the cell cycle histogram of cells treated with DMSO, colchicine or compound 10. Additionally, HeLa cells were treated with increasing concentrations of colchicine and compound 10 for 20 hours and the drug response dose curves were used to measure the mitotic arrest $IC_{50}$ for each treatment. See FIG. 3.

Figure 4A:
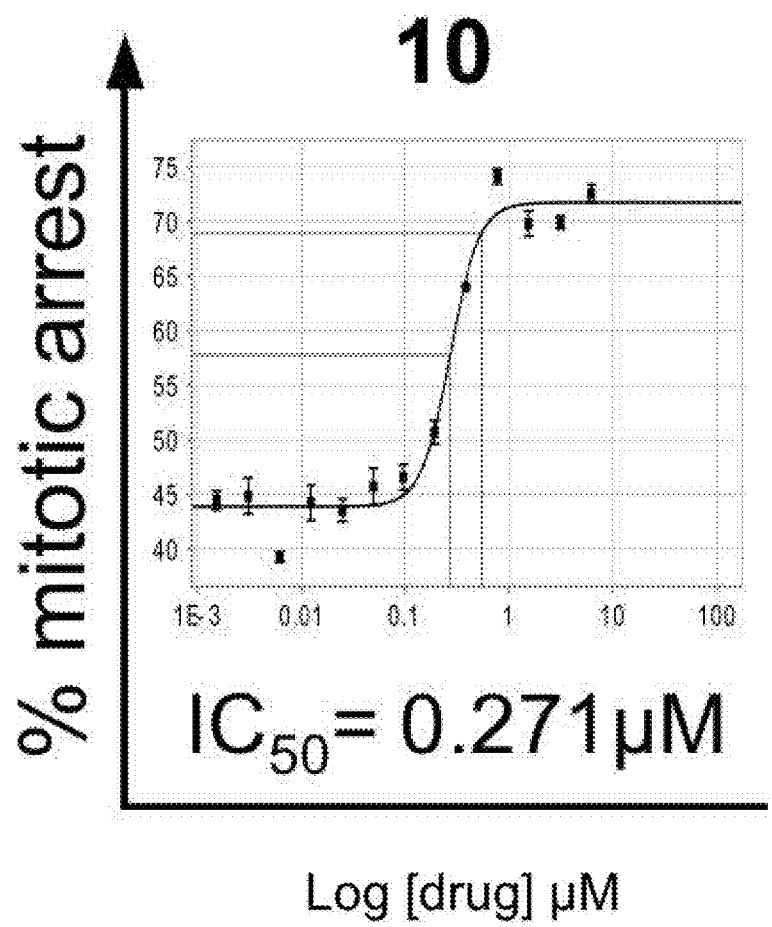
FIG. 4A shows the drug response dose curves to measure mitotic arrest $IC_{50}$s for increasing treatment with compound 10.
Figure 4B:
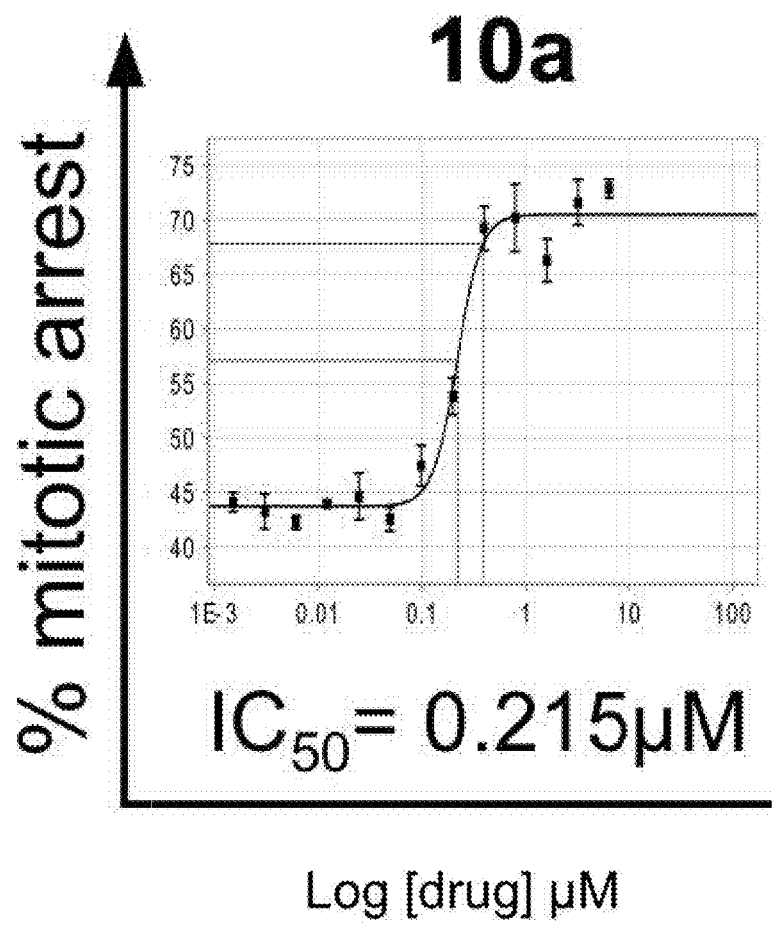
Figure 4C:
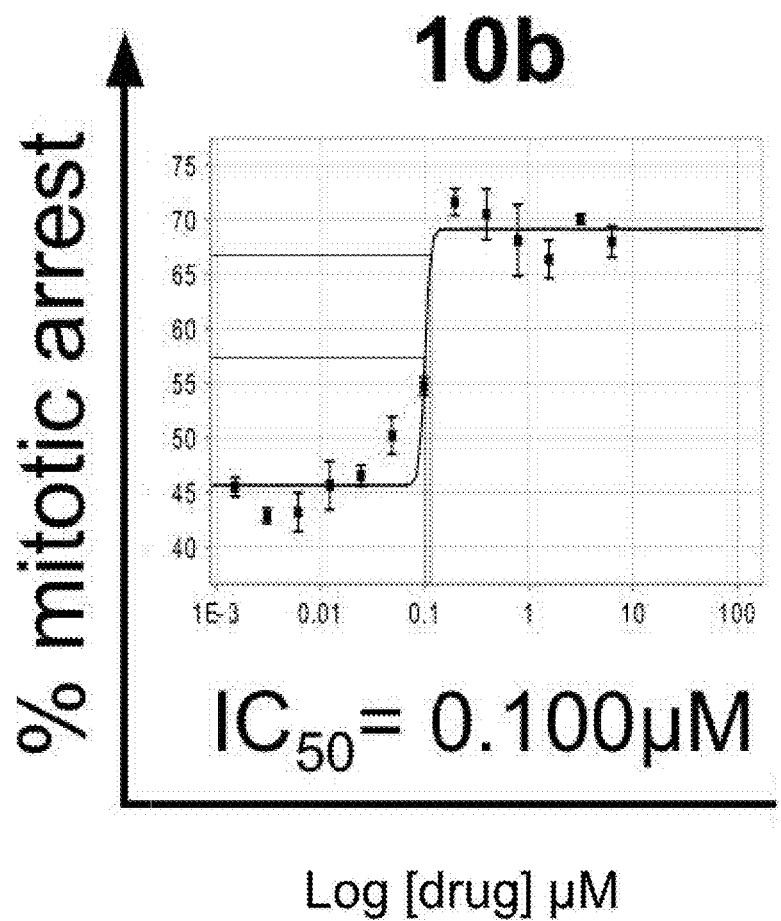
FIG. 4C shows the drug response dose curves to measure mitotic arrest IC$_{50}$s for increasing treatment with compound 10b.

Additionally, it was discovered that compound 10 and its analogs inhibit cell division and trigger apoptotic cell death. Briefly, HeLa cells were treated with increasing concentrations of 10, 10a, and 10b for 20 hours and the drug response dose curves were used to measure the mitotic arrest $IC_{50}$ for each treatment. See FIG. 4A-C. Also, the percentage of cells undergoing normal cell division was quantified for DMSO, colchicine, 10b, or taxol-treated cells. Data represent the average±SD of 3 independent experiments, with 20 cells counted for each. Asterisks denotes p-value<0.0001.

Example 5: Live-Cell Time-Lapse Microscopy

Live-cell time-lapse microscopy was carried out essentially as described by Torres et al., *Cell* 2011, 147, (6), 1309-23. Briefly, HeLa-FUCCI cells were arrested with 2 mM thymidine for eighteen hours, washed three times with PBS, and released into fresh media. Six hours postrelease, cells were treated with indicated small molecules and imaged live at 20× magnification with ten Z-stacks, one every 1 µm, for twelve hours at ten-minute intervals. Images were captured with a Leica DMI6000 microscope (Leica Microsystems), processed using LSF software and converted to Apple QuickTime movies. Each frame represents a fifteen-minute interval. Data quantitation represents the average±SD (standard deviation) of 3 independent experiments, with 20 cells counted for each.

Figure 5A:
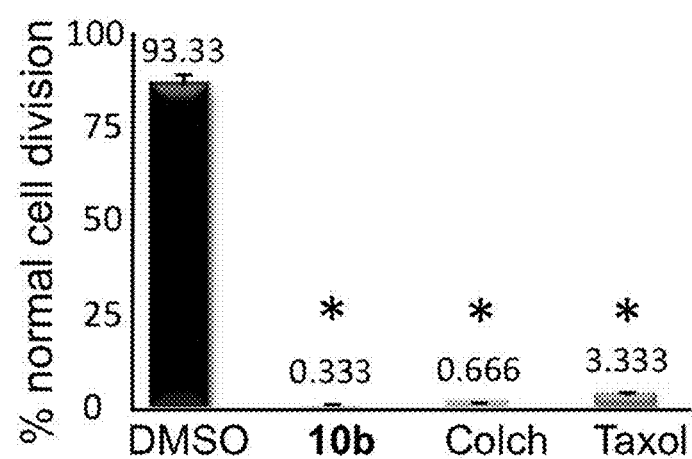
FIG. 5A quantifies the percentage of cells undergoing cell division after treatment with DMSO, colchicine, 10b, or taxol.
Figure 5B:
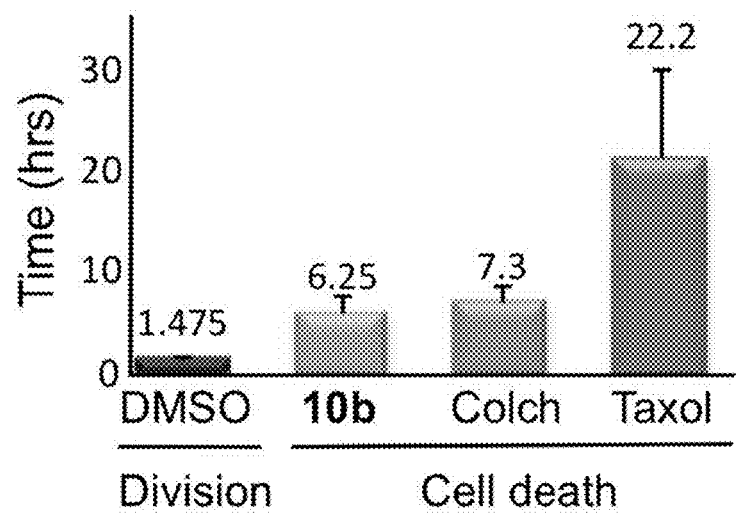
FIG. 5B quantifies the time from mitotic entry to cell death for individual cells treated with DMSO, colchicine, 10b, or taxol.
Figure 5C:
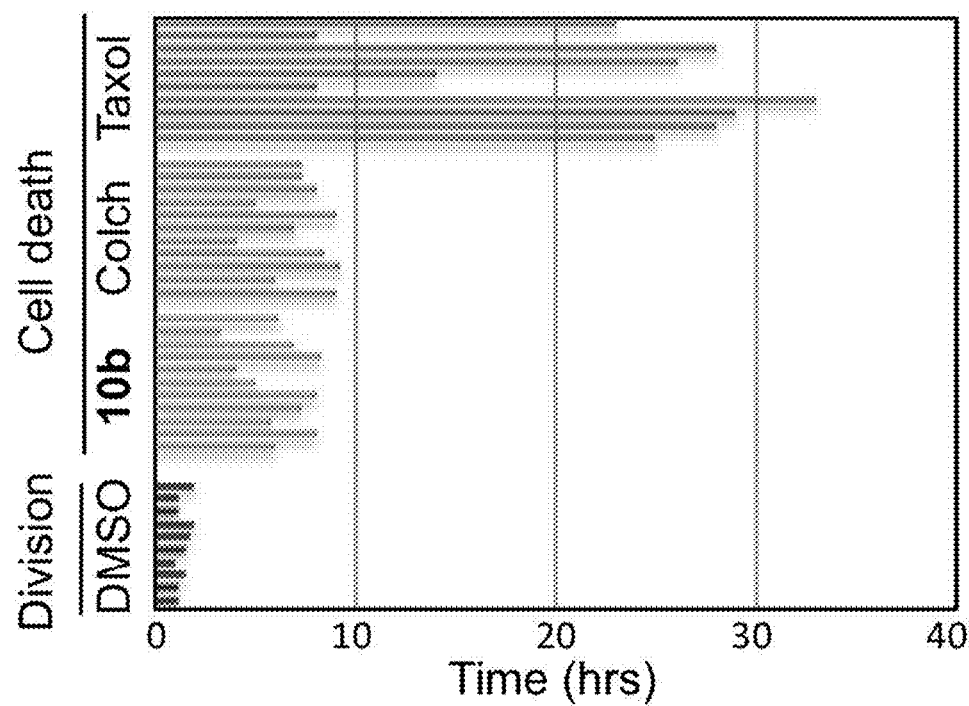
FIG. 5C quantifies the time from mitotic entry to cell death for 10 cells treated with DMSO, colchicine, 10b, or taxol.

Individual cells treated with DMSO, colchicine, 10b, or taxol were tracked over time using live-cell time-lapse microcopy and the time from mitotic entry to cell death was represented as a bar for each cell as shown in FIG. 5*b*. Additionally, the time from mitotic entry to cell death was quantified for DMSO, colchicine, 10b, or taxol-treated cells. Data represent the average±SD of 3 independent experiments, with 10 cells counted for each. See FIG. 5(*c*).

Example 6: Anticancer Agents

Figure 6C:
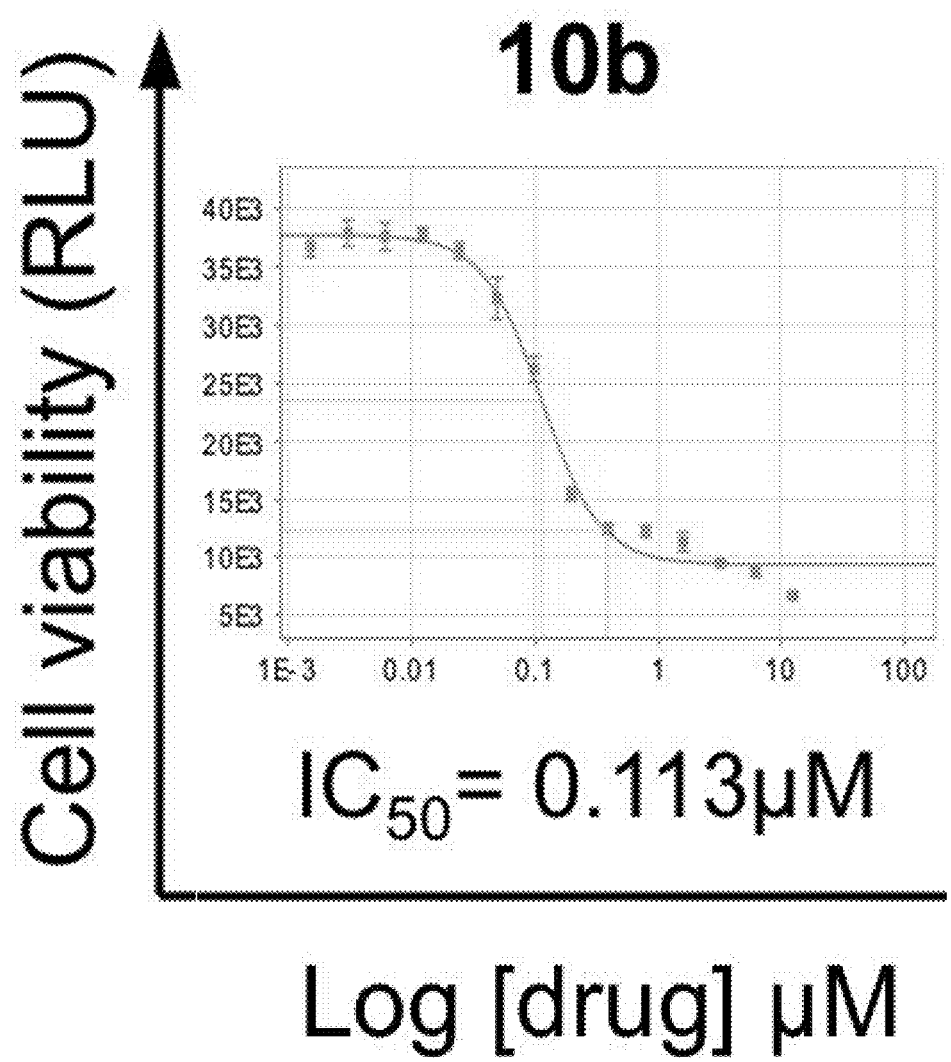
FIG. 6C shows the cell viability IC$_{50}$ for patient-derived glioblastoma cells treated with compounds 10b.

Certain compounds of the invention were shown to be potent anticancer agents. Briefly, patient-derived glioblastoma cells (HK-309) were treated with fourteen point twofold titration (1.5 nM to 12.5 µM) of 10, 10a and 10b for 72 hours and their cell viability (CellTiter-Glo Assay, Promega) $IC_{50}$ was determined. FIG. 6A-C depicts this data where RLU indicates relative light units. Interestingly, 10, 10a and 10b showed great efficacy in these populations of brain cancer cells (cell viability $IC_{50}$ for 10=352 nM, 10a=283 nM, and 10b=113 nM). These results indicated that compound 10 and its analogues were potent not only against a cervical adenocarcinoma cell line, but also patient derived glioblastoma cells.

Example 8: Functional Studies for Compounds of Formula II

Figure 10A:
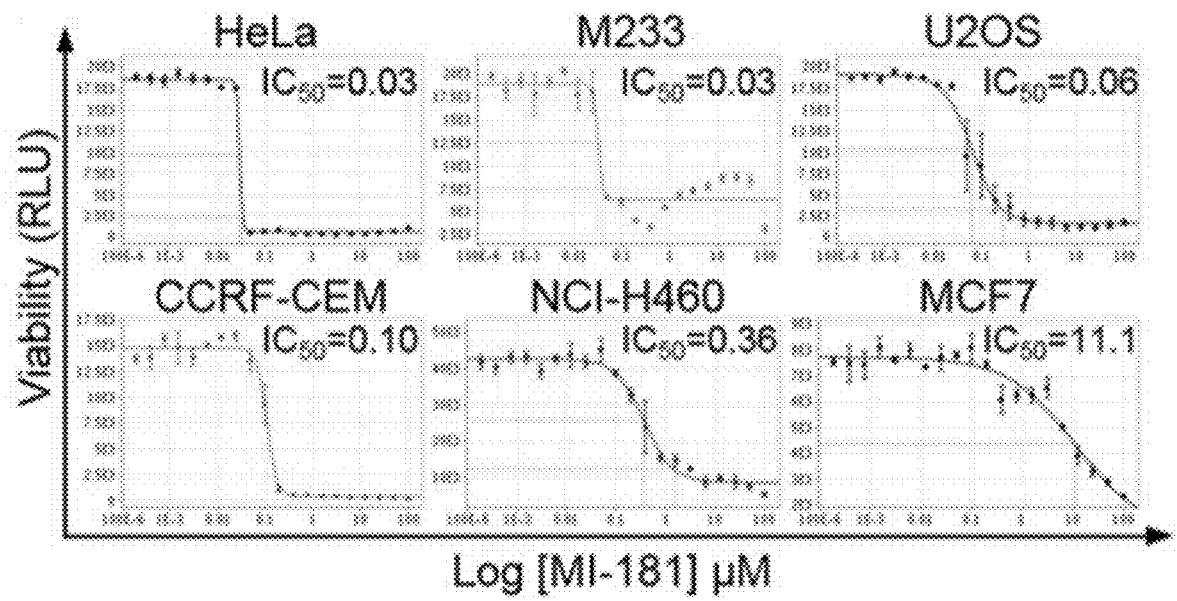
FIG. 10A shows that MI-181 is a potent cancer cell inhibitor, especially for melanomas.
Figure 10B:
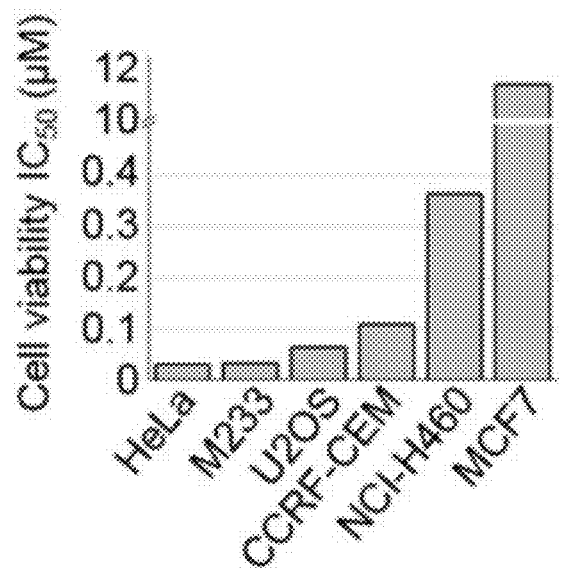
FIG. 10B shows that MI-181 is a potent cancer cell inhibitor, especially for melanomas.
Figure 10C:
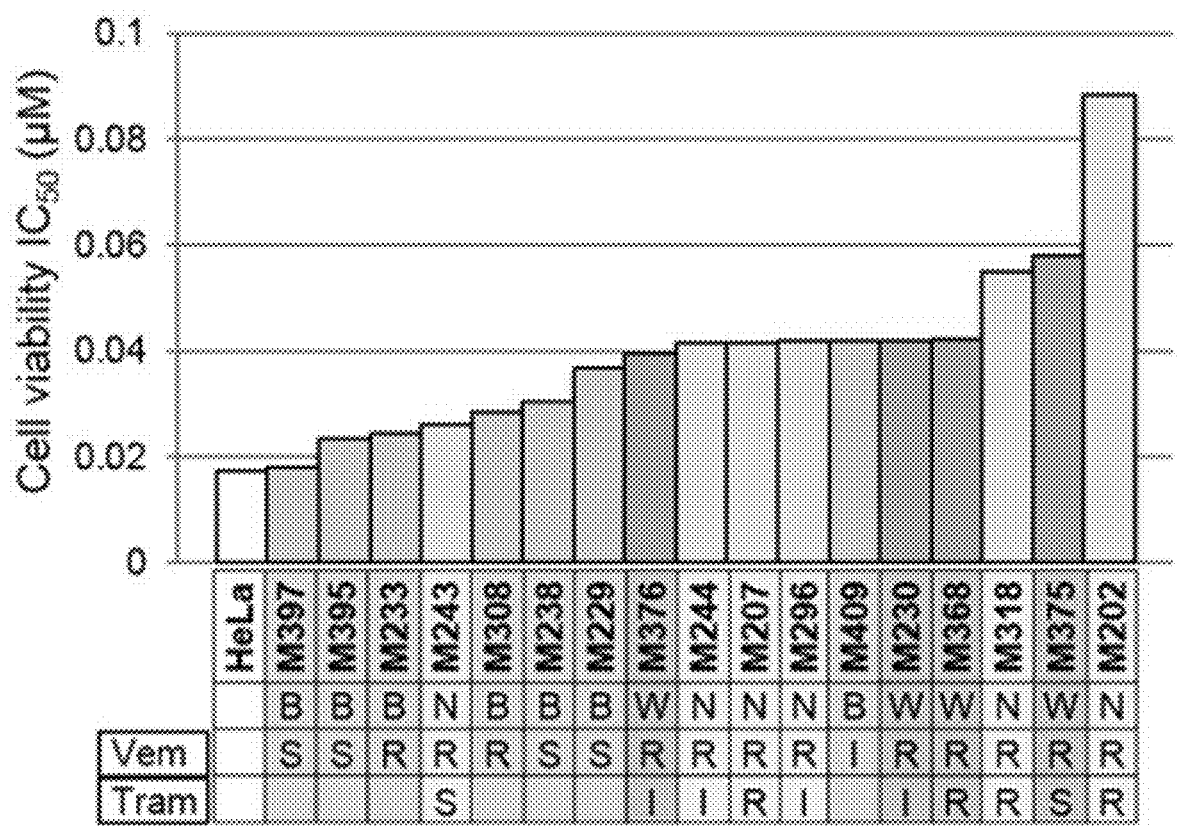
FIG. 10C shows that MI-181 is a potent cancer cell inhibitor, especially for melanomas.

To determine if MI-181 had broad anti-cancer activity, we treated a diverse panel of cancer cell lines including cervical adenocarcinoma (HeLa), breast adenocarcinoma (MCF7), melanoma (M233), osteosarcoma (U205), acute lymphoblastic leukemia (CCRF-CEM), non-small cell lung carcinoma (NCI-H460), and breast adenocarcinoma (MCF7) with MI-181 and determined its cell viability $IC_{50}$ (FIGS. 13A and 13B). Interestingly, MI-181 showed great efficacy across most cancer cell lines with a cell viability $IC_{50}$ ranging from 0.03 µM to 0.36 µM, with the exception of MCF7 cells ($IC_{50}$=11 µM) (FIGS. 13*a* and 13*b*). These results indicated that MI-181 was potent across a broad array of cancers and was most effective against cervical adenocarcinoma and melanoma cell lines. Therefore, the efficacy of MI-181 was analyzed in a panel of melanoma cell lines with defined genetic backgrounds including $BRAF^{V600E}$ and $NRAS^{Q61L}$ mutations and varied sensitivities to Vemurafenib (BRAF inhibitor) and Trametinib (MEK inhibitor), which are currently used to treat $BRAF^{V600E}$ melanomas[43,44] (FIG. 10*c*). MI-181 displayed great potency across this panel ($IC_{50}$=18 nM-90 nM) (FIG. 10*c* and Table 3). As a general trend $BRAF^{V600E}$ cell lines were slightly more sensitive than $NRAS^{Q61L}$ cell lines and MI-181 was effective in Vemurafenib and Trametinib resistant cell lines (FIG. 10*c* and Table 3). Finally, we tested the ability of MI-181 to inhibit melanoma colony formation using the M233 and M308 cell lines (both resistant to Vemurafenib). Indeed, MI-181 was a potent inhibitor of colony formation (percentage colony formation for 10 nM MI-181=0.2±0.1 and 0.8±0.7; for 10 nM colchicine=0.1±0.06 and 1.5±0.5; and for 10 nM Vemurafenib=94±7 and 102±5) (FIG. 10*d*). Thus, MI-181 is a potent inhibitor of melanoma cell lines.

TABLE 3

MI-181 $IC_{50}$ Against Various Cell Lines

| Cell Line | Cell Viability $IC_{50}$ (µM MI-181) |
|---|---|
| HeLa | 0.0174 |
| M397 | 0.0181 |
| M395 | 0.0234 |
| M233 | 0.0244 |
| M243 | 0.026 |
| M308 | 0.0283 |
| M238 | 0.0305 |
| M229 | 0.0367 |
| M376 | 0.0397 |
| M244 | 0.0415 |
| M207 | 0.0417 |
| M296 | 0.0367 |
| M409 | 0.0419 |
| M230 | 0.042 |
| M368 | 0.0421 |
| M318 | 0.0549 |

TABLE 3-continued

MI-181 IC$_{50}$ Against Various Cell Lines

| Cell Line | Cell Viability IC$_{50}$ (μM MI-181) |
|---|---|
| M375 | 0.0582 |
| M202 | 0.0883 |

Example 9: Microtubule Polymerization Assays (In Vitro Tubulin Polymerization Assays)

Figure 11:
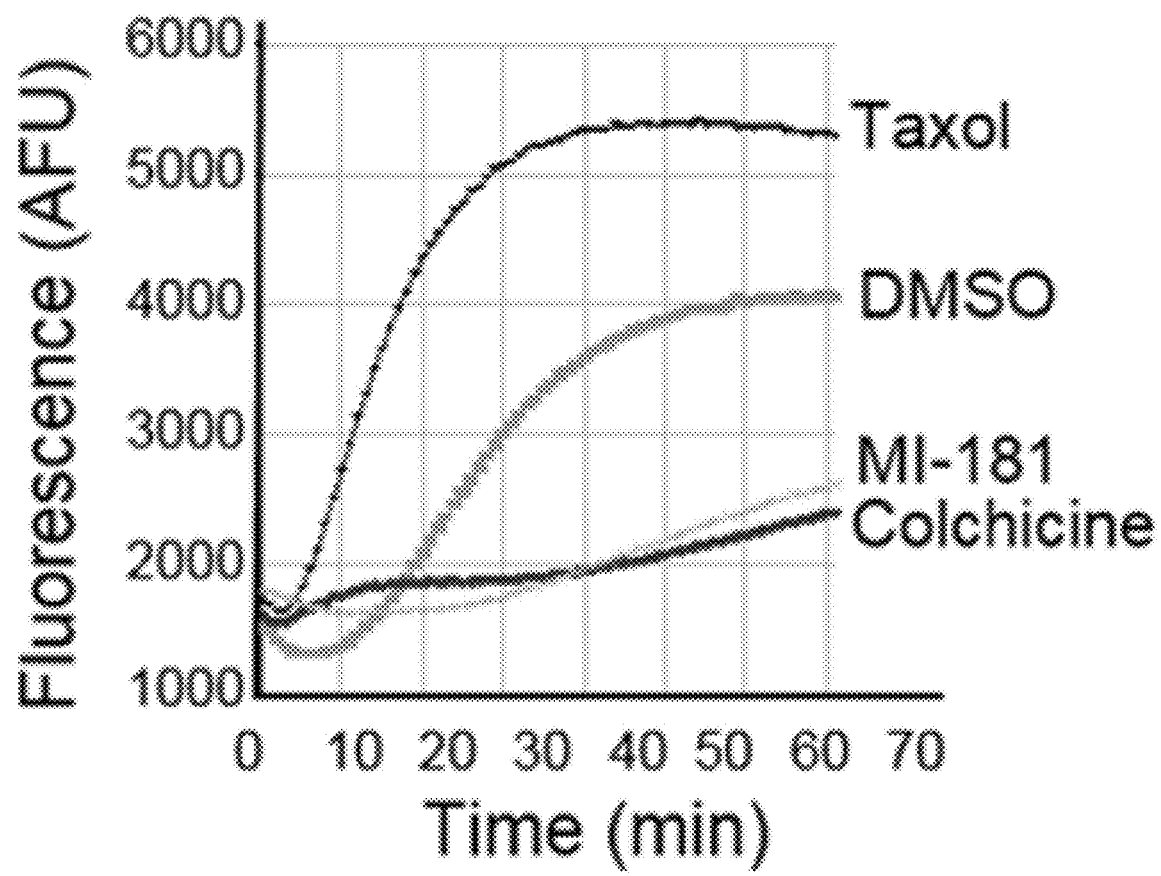
FIG. 11 shows that MI-181 inhibits tubulin polymerization.

Tubulin polymerization reactions were carried out according to the manufacturer (Cytoskeleton, BK011P) in the presence of 3 μM colchicine, MI-181, taxol or DMSO. Polymerization was monitored with a Tecan M1000 microplate reader at 420 nm for 70 minutes at 37° C. The results are depicted in FIG. 11.

Example 10: Antibodies (For Inhibition Reversibility Study, FIGS. 5 and 6)

Phospho-histone-H3-488 (Ser10) (p-H3-488, Cell Signaling), α-tubulin (Serotec), AurKB (BD Transduction), Anti-Centromere-Antibodies (ACA, Cortex Biochem), cyclin A and B (Santa Cruz Biotechnology), and SECURIN (Gene Tex). BubR1 and Bub1 were from Hongtao Yu. FITC-, Cy3- and Cy5-conjugated secondary antibodies were from Jackson Immuno Research.

Figure 8:
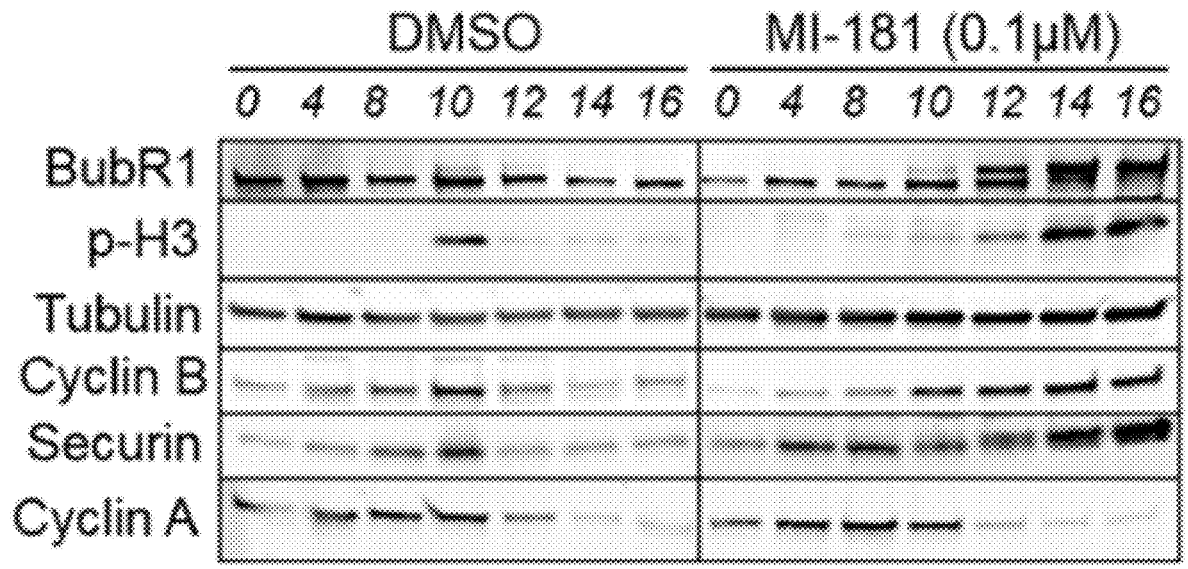
FIG. 8 shows immunoblot analysis of MI-181 treated cells.
Figure 9:
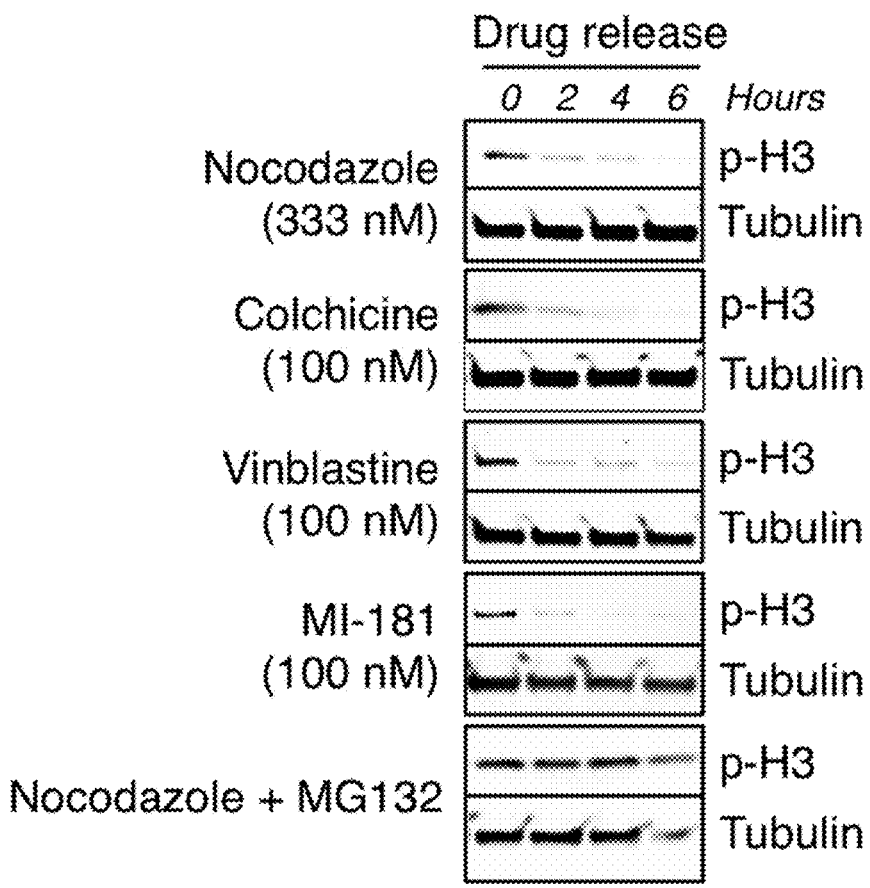
FIG. 9 shows MI-181 induced mitotic arrest is reversible.

Cells were synchronized in G1/S, released into the cell cycle in the presence of DMSO or MI-181, and cell extracts were prepared at several time points post-release. Immoblot analysis of these extracts revealed that MI-181 treated cells arrested in mitosis (p-H3 positive), activated the SAC (BubR1 remained phosphorylated) and stabilized cyclin B while degrading cyclin A. (FIG. 8). Additionally, the MI-182-induced mitotic arrest was reversible, as cells exited mitosis within 2 hours of drug washout (FIG. 9).

Example 11: Cell Cycle Analysis (High-Throughput Cell Cycle Modulator Assay)

HeLa cells were plated in 384-well plates (1500 cells/well) and treated with 10 μM drugs for 20 hours. Cells were fixed and stained with 5 μM Vybrant DyeCycle Green (Invitrogen) for 1 hour at room temperature and plates were scanned with an Acumen $^e$X3 (TTP Labtech) fluorescence cytometer using its 488 nm laser and a cell cycle histogram profile was generated for each well. For the G2/M secondary screen, 20 hours post drug addition cells were fixed with 4% paraformaldehyde, permeabilized with 0.2% Triton X-100/PBS and stained with Alexa-488-phospho-histone-H3 (Ser10, Cell Signaling) and 1 μg/ml Hoechst 33342 for 1 hour. Plates were imaged with an ImageXpress Micro (Molecular Devices) high-content fluorescence microscope. Data analysis was performed using the CDD (Collaborative Drug Discovery) software and outputs were exported to Excel. The quality of the screen was assessed by calculating the Z' factor (Z' factor=1-3×($\sigma_p+\sigma_n$)/(|$\mu_p-\mu_n$|)), which takes into account the dynamic range of the assay and variance of the data. (Zhang J. H., et al. A Simple Statistical Parameter for Use in Evaluation and Validation of High Throughput Screening Assays. *J Biomol Screen* 1999, 4(2): 67-73.) The screen performed with an average plate Z' factor of 0.51±0.09, within the optimal performance range of 0.5-1.47 (Zhang, op. cit.)

Example 12: Live-Cell Time-Lapse Microscopy

Time-lapse microscopy was performed as described in: Torres J. Z., et al. The STARD9/Kif16a Kinesin Associates with Mitotic Microtubules and Regulates Spindle Pole Assembly. *Cell* 2011, 147(6): 1309-1323. Briefly, HeLa FUCCI (fluorescent ubiquitination-based cell cycle indicator cell line, where S through M-phase cells are green due to expression of the mAG-hGeminin fusion protein, and G1-phase cells are red due to expression of the mKO2-hCdt1 fusion protein) cells were released from G1/S in the presence of indicated drug or control DMSO and ten Z-stack images (0.9 μm steps) were captured 6 hours post-release at 15-minute intervals.

Example 13: Cell Culture

Non-melanoma cell lines were purchased from ATCC, which verified identity by short-tandem repeat profiling, were passaged for less than 6 months following receipt and were maintained in F12:DMEM 50:50 medium (GIBCO) with 10% FBS, 2 mM L-glutamine and antibiotics, in 5% $CO_2$ at 37° C. Melanoma cell lines were established from patient biopsies under UCLA IRB approval #02-08-067, as described in: Sondergaard J. N., et al. Differential sensitivity of melanoma cell lines with BRAFV600E mutation to the specific Raf inhibitor PLX4032. *J Transl Med* 2010, 8: 39. Melanoma cell lines were genotyped using Oncomap3 platform for 33 genes, Affymetrix Gene Chip for SNP and IonTorrent for next-generation sequencing, were passaged for less than 6 months following verification, and were maintained in RPMI (GIBCO) with 10% FBS and antibiotics in 5% $CO_2$ at 37° C., as described previously (Sondergaard, op. cit.) For G1/S arrests, cells were treated with 2 mM thymidine (Sigma-Aldrich) for 18 hours.

Example 14: Compound Potency

For mitotic arrest IC$_{50}$s, cells were treated with a twenty-point-2-fold-titration (190 pM to 10 μM) of each compound tested for 20 hours. For cell viability IC$_{50}$s, cells were treated with a fourteen-point-2-fold-titration (12.2 nM to 100 μM). Mitotic arrest IC$_{50}$ was determined by measuring the percent G2/M arrest using the Vybrant DyeCycle Green (Invitrogen) assay described above. Cell viability IC$_{50}$ was determined using the CellTiter-Glo Assay (Promega), which measures total ATP levels. Plates were read with a Tecan M1000 micro-plate reader at 540 nm. The CDD software was used for generating IC$_{50}$ and IC$_{90}$ values.

Example 15: Crystallography

The crystal structure of tubulin bound to two ligands described here was obtained using an established system for tubulin crystal growth. (Prota A. E., Bargsten K., et al. Molecular mechanism of action of microtubule-stabilizing anticancer agents. *Science* (New York, N.Y.) 2013, 339:587-590; Prota A. E., Magiera M. M., et al. Structural basis of tubulin tyrosination by tubulin tyrosine ligase. *The Journal of Cell Biology*, 2013, 200:259-270.) Initial efforts to crystallize tubulin following an approach in which only the stathmin-like domain facilitates crystal growth never recapitulated previously described results (Gigant B., et al. The 4 A X-ray structure of a tubulin:stathmin-like domain complex. *Cell* 2000, 102:809-816; Cormier A., et al. The binding of vinca domain agents to tubulin: structural and biochemical studies. *Methods in Cell Biology* 2010, 95:373-390.)

Briefly, bovine αβ-tubulin, human RB3 or rat STMN4 stathmin-like domain, and chicken tubulin tyrosine ligase (TTL) reconstitute to form a stathmin-bound αβ-tubulin (T₂R) T₂R-TTL complex, which readily crystallizes. The inclusion of TTL enables an alternative crystal packing arrangement resulting in higher resolution diffraction data and has proven effective in studying the binding of diverse microtubule-targeting agents (Prota A. E., Bargsten K., Diaz J. F., et al. A new tubulin-binding site and pharmacophore for microtubule-destabilizing anticancer drugs. PNAS 2014, 111:13817-13821; Prota A. E., Bargsten K., Northcote P. T., et al. Structural basis of microtubule stabilization by laulimalide and peloruside A. Angewandte Chemie (Int. ed. Eng.) 2014, 53:1621-1625; Prota A. E., Danel F., et al. The novel microtubule-destabilizing drug BAL27862 binds to the colchicine site of tubulin with distinct effects on microtubule organization. J Mol Biol 2014, 426:1848-1860.)

A single crystal form grown using T₂R-TTL soaked with either MI-181 or C2 gave two crystals from which diffraction data were collected. The structure of C2 is shown below:

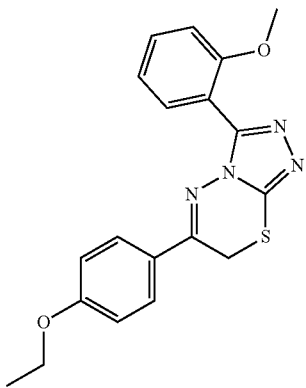 [SMILES: CCOc1ccc(C2=Nn3c(nnc3-c3ccccc3OC)SC2)cc1]

The crystal soaked with MI-181 exhibited diffraction to at least 2.60 Å and the crystal soaked with C2 diffracted to at least 3.75 Å. The final resolution cutoffs described here were determined optimally from a subset of diffraction images that took into consideration the signal-to-noise ratio for reflection intensities and the random half-data set correlation coefficient, $CC_{1/2}$ (Karplus P. A., Diederichs K. Linking crystallographic model and data quality. Science 2012, (New York, N.Y.) 336:1030-1033.)

Figure 7:
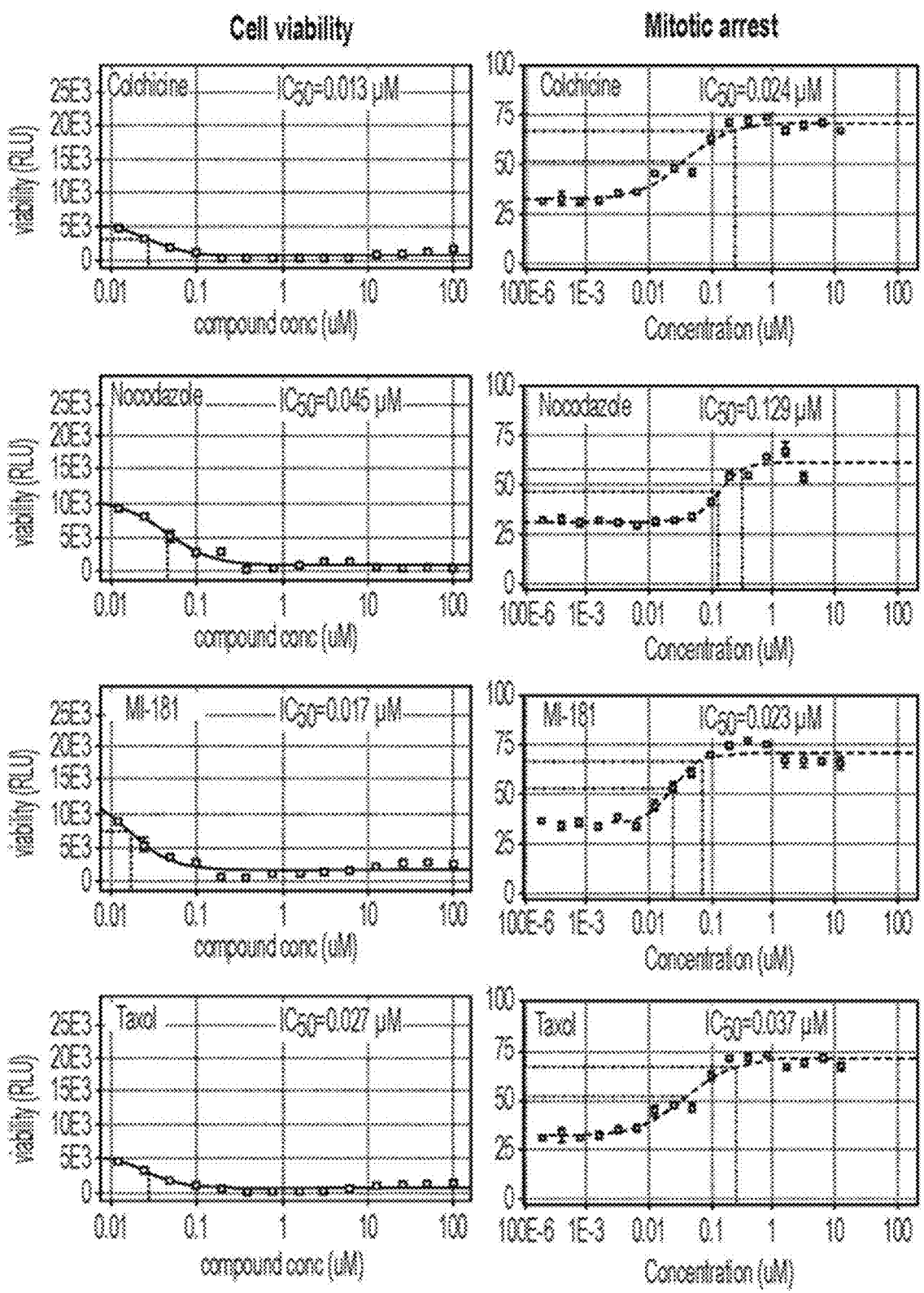
FIG. 7 shows HeLa cell mitotic arrest and cell viability dose response curves for nocodazole, colchicine, taxol and MI-181.

The T₂R-TTL structures with MI-181 and C2 bound to β-tubulin identify the previously unknown binding sites for each compound [FIGS. 7(B) and 7(C)]. Secondary structure elements and sequence numbering of tubulin are based on the initial structural studies of tubulin (Nogales E., et al. Structure of the alpha beta tubulin dimer by electron crystallography. Nature 1998, 391:199-203.). Both compounds occupy a binding pocket in the intermediate domain of β-tubulin that forms the interface with the α-subunit (residues 206-384). Other structural domains in the β-tubulin subunit include the nucleotide-binding domain (residues 1-205) and a C-terminal helical domain from residue 385 to the C-terminus. Only MI-181 is in proximity to the nucleotide-binding domain, which binds and hydrolyzes GTP within the β-subunit.

Tubulin retains a curved structure in the presence of MI-181 and C2 as observed similarly with colchicine and other molecules that interact with the expansive binding pocket on β-tubulin (Ravelli R. B., Gigant B., et al. Insight into tubulin regulation from a complex with colchicine and a stathmin-like domain. Nature 2004, 428:198-202; Dorleans A., Gigant B., et al. Variations in the colchicine-binding domain provide insight into the structural switch of tubulin. PNAS 2009, 106:13775-13779.; Prota A. E., Danel F., op. cit.) Superimposition of the taxol-stabilized straight tubulin heterodimer β-tubulin subunit with the β-tubulin subunit in our heterodimer structures indicates a rotational offset of the α-subunits. An 11° or 9° discrepancy is present depending on whether the respective analysis uses least-squares fitting or mass-weighted axes representing each heterodimer. This is in close structural agreement with the curvature observed in stathmin-bound tubulin with no depolymerizing compounds bound (Gigant B., et al., op. cit.; Lowe J., et al. Refined structure of alpha beta-tubulin at 3.5 Å resolution. J Mol Biol 2001, 313:1045-1057.) The rmsd of β-tubulin over 416 Cα atoms for each compound when superimposed on the apo-T₂R-TTL structure is 0.36 Å and 0.34 Å for MI-181 and C2, respectively (Prota A. E., Bargsten K., et al., op. cit.) These results indicate that no large structural rearrangements occur in tubulin when bound to MI-181 or C2. Additional detail is provided in McNamara, D., et al., Structures of potent anticancer compounds bound to tubulin, Protein Science vol 24:1164-1172 (2015), DOI: 10.1022/pro.2704.

Example 16: Materials and Methods

Luria-Bertani medium also known as lysogeny broth (LB) was purchased from EMD Millipore (Gibbstown, N.J.) (Bertani G. Studies on lysogenesis. I. The mode of phage liberation by lysogenic Escherichia coli. J Bacteriol 1951, 62:293-300.) Antibiotics, DNase I, and lysozyme were from Sigma Chemical Company (St. Louis, Mo.). Isopropyl β-D-1-thiogalactopyranoside (IPTG) and dithiothreitol (DTT) were from Gold Biotechnology, Inc. (St. Louis, Mo.). The compounds MI-181 and C2 (>95% purity) were purchased through MolPort (Riga, Latvia). Protease inhibitor tablets and other chemicals were from Roche and Fisher Scientific, respectively (Indianapolis, Ind. and Pittsburgh, Pa.).

The rat STMN4 stathmin-like domain with mutations Cys14Ala and Phe20Trp and chicken TTL genes were cloned into pET22b(+) (Novagen) with no additional residues or a C-terminal hexahistidine tag, respectively. The proteins were recombinantly expressed and purified using established methods (Prota A. E., Bargsten K., et al., op. cit.; Charbaut E., et al. Stathmin family proteins display specific molecular and tubulin binding properties. J Biol Chem 2001, 276:16146-16154.) Lyophilized bovine brain tubulin (>99% purity) was purchased from Cytoskeleton, Inc. (Denver, Co.), reconstituted to form T₂R-TTL complexes, and crystallized with sitting-drop vapor diffusion as described previously (Prota A. E., Bargsten K., et al., op. cit.; Prota A. E., Magiera M. M., et al., op. cit.) Crystals were soaked for 24 hours in well solution containing 1 mM compound with 10% DMSO. The crystal soaked with MI-181 was cryoprotected in Paratone-N oil and the C2_complex crystal was cryoprotected in well solution with 16% total glycerol then flash-frozen in liquid nitrogen.

Diffraction data were collected at 100K at the Advanced Photon Source (APS) Northeastern Collaborative Access Team (NECAT) beamline 24-ID-C on a DECTRIS PILATUS 6 M-F detector. The data collection and refinement statistics are reported in Table 4. Data from both crystals were processed using XDS/XSCALE (Kabsch W. Xds. Acta crystallographica Section D, Biological crystallography 2010, 66:125-132.) The program Phaser (McCoy A. J., et al.

Phaser crystallographic software. *J Appl Crystallogr* 2004, 40:658-674) was used to solve both structures by molecular replacement (MR) using a high-resolution colchicine-bound structure of $T_2R$-TTL (PDB ID 4O2B) with all non-protein atoms removed as the search model (Prota A. E., Danel F., et al., op. cit.) Both asymmetric units contain one complex of $T_2R$-TTL. Residue numbering for tubulin and stathmin are based on previously established conventions (Nogales E., et al., op. cit.; Charbaut E., et al., op. cit.) MR solutions were initially refined with rigid-body refinement using the phenix.refine module of PHENIX (Adams P. D., et al. PHENIX: building new software for automated crystallographic structure determination. *Acta crystallographica Section D, Biological crystallography* 2002, 58:1948-1954.) Ligand structures and restraints for MI-181 and C2 were generated with SMILES input for phenix.eLBOW (Moriarty N. W. et al. electronic Ligand Builder and Optimization Workbench (eLBOW): a tool for ligand coordinate and restraint generation. *Acta crystallographica Section D, Biological crystallography* 2009, 65:1074-1080) using AM1 (RM1) geometry optimization, followed by manual restraint of the ethylene linker in MI-181 to the (E)-isomer (Dewar M. J. S., et al. AM1: a new general purpose quantum mechanical molecular model. *J Am Chem Soc* 1985, 107: 3902-3909; Rocha G. B., et al. RM1: a reparameterization of AM1 for H, C, N, O, P, S, F, Cl, Br, and I. *J Comp Chem* 2006, 27:1101-1111.) Other ligands in the structures were added early in refinement after inspection of the $mF_o$-$DF_c$ difference map in Coot (Emsley P., Cowtan K. Coot: model-building tools for molecular graphics. *Acta crystallographica Section D, Biological crystallography* 2004, 60:2126-2132.)

Both structures were parameterized with individual coordinate and individual (MI-181) or grouped-per-residue (C2) isotropic atomic displacement parameter (ADP) refinement with translation liberation screw-motion (TLS) group definitions matching previous $T_2R$-TTL structure group definitions (Prota A. E., Bargsten K., et al., op. cit.; Painter J., Merritt E. A. Optimal description of a protein structure in terms of multiple groups undergoing TLS motion. *Acta crystallographica Section D, Biological crystallography* 2006, 62:439-450.) Iterative cycles of alternating refinement and model adjustment in Coot were performed using $2mF_o$-$DF_c$ and $mF_o$-$DF_c$ difference maps to obtain the final models. Residues primarily in TTL with real-space density correlation coefficients below 0.6 were omitted from the model. The coordinates of the final models and the structure factors have been deposited in the Protein Data Bank with PDB codes 4YJ2 and 4YJ3. Structures were analyzed using Chimera and PyMOL, distance measurements were calculated using β-tubulin from chain B of the structure coordinates, and all figures were prepared in PyMOL (The PyMOL Molecular Graphics System v. 1.5 (Schrodinger, LLC 2012); Pettersen E. F., et al. UCSF Chimera—a visualization system for exploratory research and analysis. *J Comp Chem* 2004, 25:1605-1612; Meng E. C., Pettersen E. F., et al. Tools for integrated sequence-structure analysis with UCSF Chimera. *BMC bioinformatics* 2006, 7:339.

TABLE 4

X-ray Data Collection and Refinement Statistics.

|  | $T_2R$-TTL MI-181 | $T_2R$-TTL C2 |
|---|---|---|
| Data collection | | |
| Space group | P $2_1$ $2_1$ $2_1$ | P $2_1$ $2_1$ $2_1$ |
| Unit cell a b c (Å), α = β = γ (°) | 104.83 157.65 181.03, 90 | 105.2 157.69 181.92, 90 |
| Resolution range (Å)[a] | 90.72-2.60 (2.69-2.60) | 91.07-3.75 (3.88-3.75) |
| Unique reflections | 92610 (9094) | 31487 (3092) |
| Multiplicity | 6.7 (6.5) | 4.4 (4.6) |
| Completeness (%) | 99.76 (98.99) | 99.25 (99.39) |
| Mean I/σ(I) | 17.89 (1.69) | 4.83 (1.40) |
| $R_{merge}$[b] | 0.076 (1.076) | 0.371 (1.404) |
| $CC_{1/2}$[c] | 0.99 (0.63) | 0.98 (0.49) |
| Res. <I/σ>~2 (Å)[c] | 2.65 | 3.90 |
| Wilson B-factor | 62.9 | 81.8 |
| Refinement | | |
| R-work/R-free (%)[d] | 18.8/23.1 | 23.9/27.9 |
| No. of non-hydrogen atoms | 17335 | 17035 |
| Macromolecules | 17000 | 16823 |
| Ligands | 224 | 196 |
| Water | 111 | 16 |
| Protein residues | 2137 | 2124 |
| RMSD(bonds) (Å) | 0.002 | 0.002 |
| RMSD(angles) (°) | 0.55 | 0.47 |
| Ramachandran favored (%)[e] | 97.0 | 96.0 |
| Ramachandran allowed (%) | 3.0 | 4.0 |
| RamachandranX allowed (%) | 0.0 | 0.0 |
| Clashscore[e] | 2.86 | 3.76 |
| Average B-factor (Å²) | 76.1 | 99.5 |
| macromolecules | 76.4 | 99.7 |
| ligands | 67.1 | 83.8 |
| solvent | 53.9 | 78.4 |
| PDB ID | 4YJ2 | 4YJ3 |

[a]Values in the highest resolution shell are shown in parenthesis.
[b]$R_{merge}$ = Σ|I − <I>|/Σ I where I is the integrated intensity of a given reflection.
[c]$CC_{1/2}$ is the random half-data set correlation coefficient (33) and the resolution at which <I/σ>~2 (Å) is given for interpretation of traditional resolution criteria.
[d]$R_{free}$ was calculated using 10% of the data.
[e]Percentages of residues in Ramachandran plot regions and clashscores, or the numbers of unfavorable all-atom steric overlaps ≥0.4 Å per 1000 atoms, were determined using MolProbity (58).

Example 17: Anticancer Agents

Certain compounds of Formula II, such as MI-181, were shown to be potent anticancer agents.

INCORPORATED BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

The invention claimed is:

1. A method for treating melanoma or cervical adenocarcinoma in a subject in need thereof, comprising administering to the subject an effective amount of

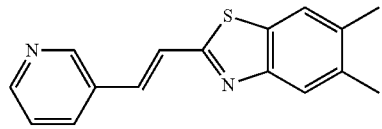 [SMILES: Cc1cc2nc(/C=C/c3cccnc3)sc2cc1C]

or a pharmaceutically acceptable salt thereof.

2. The method of claim 1, wherein the cancer is a melanoma.

3. The method of claim 2, wherein the melanoma is selected from lentigo maligna melanoma, superficial spreading melanoma, acral lentiginous melanoma, mucosal melanoma, nodular melanoma, polypoid melanoma, desmoplastic melanoma, amelanotic melanoma, soft-tissue melanoma, melanoma with small nevus-like cells, melanoma with features of a Spitz nevus, and uveal melanoma.

4. The method of claim 1, wherein the cancer is a cervical adenocarcinoma.

* * * * *